United States Patent
Blumenkranz

(10) Patent No.: US 8,491,574 B2
(45) Date of Patent: Jul. 23, 2013

(54) POLARIZATION AND TEMPERATURE INSENSITIVE SURGICAL INSTRUMENT FORCE TRANSDUCER

(75) Inventor: Stephen J. Blumenkranz, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 986 days.

(21) Appl. No.: 12/541,848

(22) Filed: Aug. 14, 2009

(65) Prior Publication Data

US 2010/0298844 A1   Nov. 25, 2010

Related U.S. Application Data

(63) Continuation-in-part of application No. 12/414,534, filed on Mar. 30, 2009.

(51) Int. Cl.
    *A61B 19/00* (2006.01)

(52) U.S. Cl.
    USPC .............................................. 606/1; 606/130

(58) Field of Classification Search
    USPC ............................................................ 606/1
    See application file for complete search history.

(56) References Cited

U.S. PATENT DOCUMENTS

| | | | | |
|---|---|---|---|---|
| 6,393,181 | B1 * | 5/2002 | Bulman et al. | 385/37 |
| 6,470,205 | B2 * | 10/2002 | Bosselmann et al. | 600/424 |
| 6,584,248 | B2 * | 6/2003 | Franzen et al. | 385/37 |
| 7,068,869 | B1 | 6/2006 | Araujo et al. | |
| 7,173,696 | B2 | 2/2007 | Taverner et al. | |
| 7,930,065 | B2 * | 4/2011 | Larkin et al. | 700/245 |
| 2001/0021843 | A1 * | 9/2001 | Bosselmann et al. | 606/2 |
| 2002/0176647 | A1 * | 11/2002 | Spirin et al. | 385/12 |
| 2007/0060847 | A1 * | 3/2007 | Leo et al. | 600/587 |
| 2007/0151390 | A1 | 7/2007 | Blumenkranz et al. | |
| 2007/0151391 | A1 | 7/2007 | Larkin et al. | |
| 2008/0065100 | A1 * | 3/2008 | Larkin | 606/130 |
| 2008/0065111 | A1 | 3/2008 | Blumenkranz et al. | |
| 2008/0297808 | A1 * | 12/2008 | Riza et al. | 356/503 |
| 2009/0157092 | A1 | 6/2009 | Blumenkranz et al. | |
| 2009/0177095 | A1 | 7/2009 | Aeby et al. | |
| 2009/0192522 | A1 | 7/2009 | Blumenkranz | |

(Continued)

FOREIGN PATENT DOCUMENTS

WO    WO2007015139 A2    2/2007

OTHER PUBLICATIONS

Packaging Effects on Fiber Bragg Grating Sensor Performance; Hao et al.; ACTA Automatica SINICA, Nov. 2006.*

(Continued)

*Primary Examiner* — Henry M Johnson, III

(57) ABSTRACT

A force sensor apparatus, operatively mounted in a surgical instrument includes the force transducer. The force transducer includes a transducer body having a coefficient of thermal expansion, and at least one optic fiber, fixedly attached to the transducer body, including a Bragg grating; and having a coefficient of thermal expansion matched to the coefficient of thermal expansion of the transducer body to mitigate polarization and calibration drift effects on the force transducer. The transducer body comprises a metal transducer body, and the metal transducer body is selected from a group of metal bodies including an aluminum alloy transducer body, a stainless steel alloy transducer body, a maraging steel alloy transducer body, and a titanium alloy transducer body. The at least one optic fiber comprises an optic fiber having a negative thermo-optic coefficient, such as a phosphate glass optic fiber reducing the thermal sensitivity of the transducer.

11 Claims, 23 Drawing Sheets

U.S. PATENT DOCUMENTS

2010/0114115 A1* 5/2010 Schlesinger et al. .......... 606/130
2011/0048136 A1* 3/2011 Birch et al. ...................... 73/705
2011/0087112 A1* 4/2011 Leo et al. ...................... 600/478

OTHER PUBLICATIONS

AK Steel, "15-5PH Stainless Steel," Product Data Sheet, UNS S15500, 2 pages, 2007.
AK Steel, "17-4PH Stainless Steel," Product Data Sheet, UNS S17400, 2 pages, 2007.
AK Steel, "17-7PH Stainless Steel," Product Data Sheet, UNS S17700, 2 pages, 2007.
AK Steel, "PH15-7Mo Stainless Steel," Product Data Sheet, UNS S15700, 2 pages, 2007.
Albert, J. et al., "Strong Bragg gratings in phosphate glass single mode fiber," Applied Physics Letters, 2006, vol. 89, pp. 101127-1-101127-3.
Alcoa Aluminum, "7055 Alloy-T7751 Plate and-T77511 Extrusions," Technical Data Sheet, 2 pages, Downloaded Jul. 31, 2009, Internet: www.millproducts-alcoa.com.
Alcoa Aluminum, "Understanding Cold Finished Aluminum Alloys: Alloy 7075," Technical Data Sheet, 2 pages, May 2004. Internet: www.alcoa.com/gcfp.
Alcoa Distribution and Industrial Products, "Alloy 6061: Understanding Extruded Aluminum Alloys," 2002, 2 pages; Internet: http://www.galcit.caltech.edu/~tongc/html/data/elastic/Extruded_Alloy_6061.pdf.
Allvac, "Vascomax® Nickel Maraging Alloys," Technical Data Sheet, 9 pages, 2000.
ASM Aerospace Specification Metals Inc., "Titanium Ti-3Al-2.5V, St 925° C., Aged 480° C.," UNS No. R56320, Material Data Sheet, 2 pages, Downloaded Jun. 29, 2009, Internet: http://asm.matweb.com/search/SpecificMaterial.asp?bassnum=MTA322.
ASM Aerospace Specification Metals Inc., "Titanium Ti-5Al-2.5Sn," UNS No. R54520, Material Data Sheet, 2 pages, Downloaded Jun. 29, 2009, Internet: http://asm.matweb.com/search/SpecificMaterial.asp?bassnum=MTA520.
ATI Allvac, "ATI Titanium 6Al-2Sn-4Zr-2Mo Alloy," UNS No. R54620,1; Technical Data Sheet, 3 pages, Mar. 21, 2008.
ATI Allvac, "ATI Titanium 6Al-4V ELI Alloy," UNS No. R56401; Technical Data Sheet, 3 pages, Mar. 21, 2008.
ATI Allvac, "ATI Titanium 6Al-6V-2Sn Alloy," UNS No. R56620; Technical Data Sheet, 3 pages, Mar. 21, 2008.
ATI Defense, "Maraging Steels for Defense: ATI C-200™/C-250™/C-300™/C-350™ Alloys," Technical Data Sheet, 10 pages, Jan. 12, 2009.
Carpenter Technology Corporation, "Alloy Data: Carpenter Stainless Type 410," UNS No. S41000, Technical Data Sheet, 6 pages, May 1, 1987 Edition, Internet: http://cartech.ides.com/datasheet.aspx?i=103&e=82&c=TechArt&FMT=PRINT.
Carpenter Technology Corporation, "Alloy Data: Carpenter Stainless Type 420," UNS No. S42000, Technical Data Sheet, 6 pages, Sep. 1, 1986 Edition, Internet: http://cartech.ides.com/datasheet.aspx?i=103&e=77&c=TechArt&FMT=PRINT.
Carpenter Technology Corporation, "Alloy Data: Carpenter Stainless Type 440A," UNS No. S44002, Technical Data Sheet, 5 pages, Apr. 1, 1987 Edition, Internet: http://cartech.ides.com/datasheet.aspx?i=103&e=74&c=TechArt&FMT=PRINT.
Carpenter Technology Corporation, "Alloy Data: Carpenter Stainless Type 440B," UNS No. S44003, Technical Data Sheet, 4 pages, Apr. 1, 1987 Edition, Internet: http://cartech.ides.com/datasheet.aspx?i=103&e=73&c=TechArt&FMT=PRINT.
Carpenter Technology Corporation, "Alloy Data: Carpenter Stainless Type 440C," UNS No. S44004, Technical Data Sheet, 5 pages, Jun. 1, 1987 Edition, Internet: http://cartech.ides.com/datasheet.aspx?i=103&e=72&c=TechArt&FMT=PRINT.
Carpenter Technology Corporation, "Alloy Data: Carpenter 13-8 Stainless," Technical Data Sheet, UNS No. S13800,10 pages, Oct. 14, 2004 Edition, Internet: http://cartech.ides.com/datasheet.aspx?i=103&e=51&c=TechArt&FMT=PRINT.
Carpenter Technology Corporation, "Carpenter AerMet® 100 Alloy," UNS No. K92580, Technical Data Sheet, 10 pages, Sep. 1, 1995 Edition, Internet: http://cartech.ides.com/datasheet.aspx?E=161&FMT=PRINT.
Carpenter Technology Corporation, "Carpenter AerMet® 310 Alloy," Technical Data Sheet, 3 pages, Sep. 20, 2007 Edition, Internet: http://cartech.ides.com/datasheet.aspx?E=158&FMT=PRINT.
Carpenter Technology Corporation, "Carpenter AerMet® 340 Alloy," Technical Data Sheet, 6 pages, May 11, 2007 Edition, Internet: http://cartech.ides.com/datasheet.aspx?E=338&FMT=PRINT.
Carpenter Technology Corporation, "Carpenter Stainless Type 416 (No. 5)," UNS No. S41600, Technical Data Sheet, 5 pages, Sep. 1, 1986 Edition, Internet: http://cartech.ides.com/datasheet.aspx?&E=79&CK841002&FMT=PRINT.
Carpenter Technology Corporation, "Custom 450® Stainless," Technical Data Sheet, UNS S45000, 14 pages, Aug. 1, 1994 Edition, Internet: http://cartech.ides.com/datasheet.aspx?E=57&FMT=PRINT.
Carpenter Technology Corporation, "Custom 455® Stainless," Technical Data Sheet, UNS S45500, 12 pages, Jun. 9, 2006 Edition, Internet: http://cartech.ides.com/datasheet.aspx?E=56&FMT=PRINT.
Carpenter Technology Corporation, "Custom 465® Stainless," Technical Data Sheet, 16 pages, Jan. 8, 2008 Edition, Internet: http://cartech.ides.com/datasheet.aspx?E=55&FMT=PRINT.
Carpenter Technology Corporation, "Custom 475® Stainless," Technical Data Sheet, 5 pages, Mar. 4, 2009 Edition, Internet: http://cartech.ides.com/datasheet.aspx?i=103&e=326&c=TechArt&FMT=PRINT.
Cepolina F. et al., "Review of robotic fixtures for minimally invasive surgery," International Journal of Medical Robotics and Computer Assisted Surgery, 2004, pp. 43-63, vol. 1, Issue-1.
Corning Incorporated, Corning® SMF-28e® Optical Fiber Product Information Data Sheet, PI1344, May 2007, 4 pages.
Kaiser Aluminum, "Rod & Bar Alloy 6033," Technical Data Sheet , 2 pages, downloaded May 28, 2009, Internet: www.kaiseraluminum.com.
Kaiser Aluminum, "Rod & Bar Alloy 6041," Technical Data Sheet, Doc. No. 1015, Revised May 24, 2007, 2 pages.
Kaiser Aluminum, "Rod & Bar Alloy 6262," Technical Data Sheet, 2 pages, Revised May 2006, Internet: www.kaiseraluminum.com.
Kaiser Aluminum, "Rod & Bar Alloy 7050," Technical Data Sheet, 2 pages, Revised May 2006.
Kaiser Aluminum, "Rod & Bar Alloy 7068," Technical Data Sheet, 2 pages, Revised May 2006.
Kaiser Aluminum, "Rod & Bar Alloy 7075," Technical Data Sheet, 2 pages, Revised May 2006.
Kaiser Aluminum, "Rod & Bar Alloy 7X49," Technical Data Sheet, Revised May 2006, 2 pages.
Matter Project, "aluSelect Mechanical Properties: EN AW-7010," 1 page, 2001, Internet: http://aluminium.matter.org.uk/aluselect/09_mech_browse.asp.
MATWEB Online Materials Database, "Aluminum 2014-T6; 2014-T651," Material Data Sheet, 3 pages, downloaded Jul. 29, 2007; Internet: http://www.matweb.com/search/SpecificMaterialPrint.asp?bassnum=MA2014T6.
MATWEB Online Materials Database, "Aluminum 2024-T3," Material Data Sheet, 2 pages, downloaded Jul. 29, 2007; Internet: http://www.matweb.com/search/SpecificMaterialPrint.asp?bassnum=MA2024T3.
MATWEB Online Materials Database, "Aluminum 2024-T361," Material Data Sheet, 2 pages, downloaded Jul. 29, 2007; Internet: http://www.matweb.com/search/SpecificMaterialPrint.asp?bassnum=MA2024T361.
MATWEB Online Materials Database, "Aluminum 2024-T851," Material Data Sheet, 2 pages, downloaded Jul. 29, 2007; Internet: http://www.matweb.com/search/SpecificMaterialPrintasp?bassnum=MA2024T851.
MATWEB Online Materials Database, "Aluminum 2048," Material Data Sheet, 2 pages, downloaded Jul. 29, 2007; Internet: http://www.matweb.com/search/SpecificMaterialPrint.asp?bassnum=MA2048.

MATWEB Online Materials Database, "Aluminum 2090-T83," Material Data Sheet, 2 pages, downloaded Jul. 29, 2007; Internet: http://www.matweb.com/search/SpecificMaterialPrint.asp?bassnum=MA2090T83.

MATWEB Online Materials Database, "Aluminum 2090-T86," Material Data Sheet, 2 pages, downloaded Jul. 29, 2007; Internet: http://www.matweb.com/search/SpecificMaterialPrint.asp?bassnum=MA2090T86.

MATWEB Online Materials Database, "Aluminum 2091-T8x, 10% cold work," Material Data Sheet, 2 pages, downloaded Jul. 29, 2007; Internet: http://www.matweb.com/search/SpecificMaterialPrint.asp?bassnum=MA2091T8A.

MATWEB Online Materials Database, "Aluminum 2124-T851" Material Data Sheet, 2 pages, downloaded Jul. 29, 2007; Internet: http://www.matweb.com/search/SpecificMaterialPrint.asp?bassnum=MA2124T851.

MATWEB Online Materials Database, "Aluminum 6061-T6; 6061-T651," Material Data Sheet, 2 pages, downloaded Apr. 6, 2006, Internet: http://www.matweb.com/search/SpecificMaterialPrint.asp?bassnum=MA6016.

MATWEB Online Materials Database, "Aluminum 6066-T6; 6066-T651," Material Data sheet, 2 pages, downloaded Sep. 13, 2007, Internet: http://www.matweb.com/search/SpecificMaterialPrint.asp?bassnum=MA6066T6.

MATWEB Online Materials Database, "Aluminum 7001-T6; 7001-T651," Material Data Sheet, 2 pages, downloaded Jul. 29, 2007, Internet: http://www.matweb.com/search/SpecificMaterialPrint.asp?bassnum=MA7001T6.

MATWEB Online Materials Database, "Aluminum 7049-T73; 7049-T7352," Material Data Sheet, 2 pages, Downloaded Jul. 29, 2007, Internet: http://www.matweb.com/search/SpecificMaterialPrint.asp?bassnum=MA7049T73.

MATWEB Online Materials Database, "Aluminum 7076-T61," Material Data Sheet, 2 pages, downloaded Jul. 29, 2007, Internet: http://www.matweb.com/search/SpecificMaterialPrint.asp?bassnum=MA7076T61.

MATWEB Online Materials Database, "Aluminum 7175-T66," Material Data Sheet, 2 pages, Downloaded Jul. 29, 2007, Internet: http://www.matweb.com/search/SpecificMaterialPrint.asp?bassnum=MA7175T66.

MATWEB Online Materials Database, "Aluminum 7178-T6; 7178-T651," Material Data Sheet, 2 pages, Downloaded Jul. 29, 2007, Internet: http://www.matweb.com/search/SpecificMaterialPrint.asp?bassnum=MA7178T6.

MATWEB Online Materials Database, "Aluminum 7475-1651," Material Data Sheet, 2 pages, Downloaded Jul. 29, 2007, Internet: http://www.matweb.com/search/SpecificMaterialPrint.asp?bassnum=MA7475T651.

MATWEB Online Materials Database, "RSP Technology Aluminum RSA-706 T6," Material Data Sheet, 1 page, Downloaded Jul. 29, 2007, Internet: http://www.matweb.com/search/SpecificMaterialPrint.asp?bassnum=NRSP09.

MATWEB Online Materials Database, "RSP Technology Aluminum RSA-708 High Strength Alloy," Material Data Sheet, 1 page, Downloaded Jul. 29, 2007, Internet: http://www.matweb.com/search/SpecificMaterialPrint.asp?bassnum=NRSP14.

MATWEB Online Materials Database, "RSP Technology Aluminum RSA-708 T6," Material Data Sheet, 1 page, Downloaded Jul. 29, 2007, Internet: http://www.matweb.com/search/SpecificMaterialPrint.asp?bassnum=NRSP10.

MATWEB Online Materials Database, "RSP Technology Aluminum RSP-709 High Strength Alloy, (RSA-708 according to RSP's datasheets)," Material Data Sheet, 1 page, Downloaded Jul. 29, 2007, Internet: http://www.matweb.com/search/SpecificMaterialPrint.asp?bassnum=NRSP15.

MATWEB Online Materials Database, "Titanium Beta C (Ti-3Al-8V-6Cr-4Mo-4Zr ST 815° C., Aged 425° C.," Material Data Sheet, 1 page, Jun. 17, 2009.

Questek® Innovations LLC, "Ferrium® S53: Corrosion Resistant Ultrahigh-Strength Steel for Aerospace Structural Applications," Technical Data Sheet, 2 pages, Apr. 2008.

RSP Technology, "RSP High Strength Alloys," Datasheet, 1 page, Downloaded Jul. 30, 2007, Internet: www.rsp-technology.com.

Schafer Lightweight Optical Systems, Data Sheet for "Phosphate Athermal Glass for Windows and Fibers," 2006, 14 pages; Internet: http://optics.nasa.gov/tech_days/tech_days_2006/docs/36%20Schafer%20Phosphate%20Athermal%20Glass%20fo-%20Windows%20and%20Fibers.pdf.

Spotwelding Consultants, Inc., "GlidCop Dispersion Strengthened Copper, GlidCop AL-60," Technical Data Sheet C15760, 2 pages, Feb. 19, 2006.

The Aluminum Association, Inc., "International Alloy Designations and Chemical Composition Limits for Wrought Aluminum and Wrought Aluminum Alloys," Registration Record Series: Teal Sheets, Feb. 2009, 37 pages.

Timet, "Timetal 6-2-4-6 High-Strength Intermediate Temperature Alloy," Technical Data Sheet, 2 pages, 2000.

Vertut, Jean and Phillipe Coiffet, Robot Technology: Teleoperation and Robotics Evolution and Development, English translation Prentice-Hall, Inc., Inglewood Cliffs, NJ, USA 1986, vol. 3A, 332 pages.

PCT/US10/45274 International Search Report and Written Opinion of the International Searching Authority, mailed Dec. 7, 2010, 9 pages.

* cited by examiner

FIG. 5C1

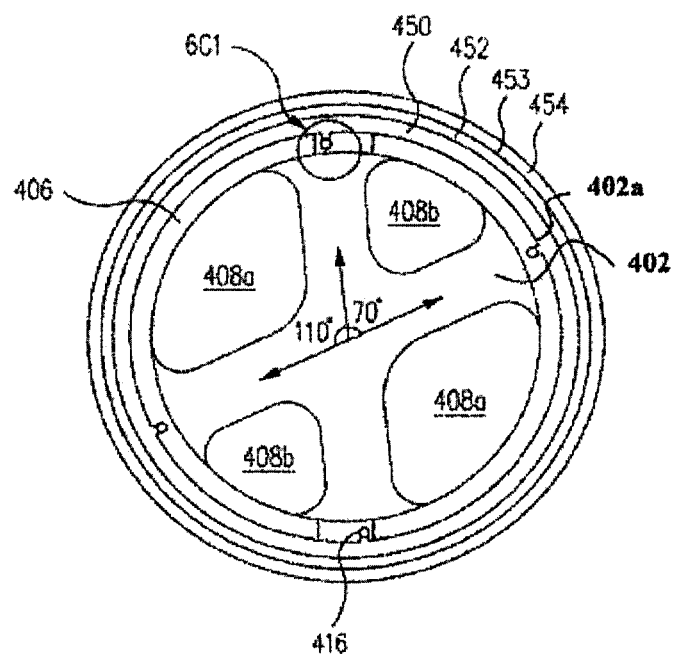
FIG. 6C
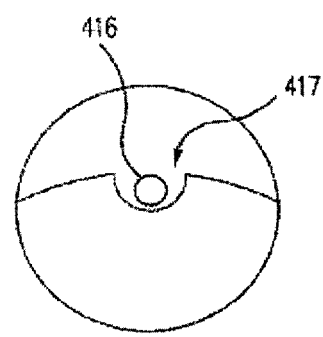
FIG. 6C1

FIG. 7B1

POLARIZATION AND TEMPERATURE INSENSITIVE SURGICAL INSTRUMENT FORCE TRANSDUCER

CROSS-REFERENCE TO RELATED APPLICATION

This application is a continuation-in-part of U.S. application Ser. No. 12/414,534, filed Mar. 30, 2009, which is incorporated by reference herein in its entirety for all purposes.

TECHNICAL FIELD

The present invention relates generally to minimally-invasive surgical systems, e.g., teleoperated robotic surgical systems, and, more particularly, to an improved system, apparatus, and method for sensing forces applied to a surgical instrument.

BACKGROUND

In robotically-assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces, or the like, which are operatively coupled to the surgical instruments through a controller with servo motors for articulating the instruments' position and orientation at the surgical site. The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves (cannulas) inserted through incisions into a body cavity, such as the patient's abdomen. There are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, dissecting, cauterizing, coagulating tissue, etc. A surgeon may employ a large number of different surgical instruments/tools during a procedure.

This new surgical method through remote manipulation has created many new challenges. One such challenge is providing the surgeon with the ability to accurately "feel" the tissue that is being manipulated by the surgical instrument via the robotic manipulator. The surgeon must rely on visual indications of the forces applied by the instruments or sutures. It is desirable to sense the forces and torques applied to the tip of the instrument, such as an end effector (e.g., jaws, grasper, blades, etc.) of robotic minimally invasive surgical instruments, in order to feed the forces and torques back to the surgeon user through the system hand controls or by other means, such as visual display, vibrations, or audible tone. One device for this purpose from the laboratory of G. Hirzinger at DLR Institute of Robotics and Mechatronics is described in "Review of Fixtures for Low-Invasiveness Surgery" by F. Cepolina and R. C. Michelini, *Int'l Journal of Medical Robotics and Computer Assisted Surgery*, Vol. 1, Issue 1, page 58, the contents of which are incorporated by reference herein for all purposes. However, that design disadvantageously places a force sensor distal to (or outboard of) the wrist joints, thus requiring wires or optic fibers to be routed through the flexing wrist joint and also requiring the yaw and grip axes to be on separate pivot axes.

Another problem has been fitting and positioning the necessary wires, rods, or tubes for mechanical actuation of end effectors in as small a space as possible because relatively small instruments are typically desirable for performing surgery.

Furthermore, the temperature sensitivity of force sensors has caused problems with providing accurate force measurements.

What is needed, therefore, are improved telerobotic systems, surgical apparatus, and methods for remotely controlling surgical instruments at a surgical site on a patient. In particular, these systems and methods should be configured to provide accurate feedback of forces and torques to the surgeon to improve user awareness and control of the instruments.

SUMMARY

The present invention provides an apparatus, system, and method for improving force and torque feedback to and sensing by a surgeon performing a robotic surgery. In one embodiment, a force sensor includes a tube portion that includes a plurality of radial ribs and a strain gauge or gauges positioned over each of the plurality of radial ribs. A proximal part of the tube portion is coupled to a shaft of a surgical instrument that may be operably coupled to a manipulator arm of a robotic surgical system. A distal part of the tube portion is coupled to a wrist joint coupled to an end effector. The couplings may be direct or indirect with an intermediate mechanical component between the coupled parts.

Groups of strain gauges are positioned on or near a distal end of an instrument shaft proximal to (i.e., inboard of) a moveable wrist of a robotic surgical instrument via an apparatus that senses forces and torques at the distal tip of the instrument without errors due to changes in the configuration of the tip (such as with a moveable wrist) or steady state temperature variations.

The force sensor apparatus may be comprised of advantageous materials, such as high thermal diffusivity material and negative or differing thermo-optic coefficient optical fiber materials, high coefficient of thermal expansion optic fiber materials, and/or include thermal shielding/heat spreading designs to provide accurate force signals even under asymmetric transient thermal loads that may occur in surgery.

Advantageously, the present invention improves the sensing and feedback of forces to the surgeon and substantially eliminates the problem of passing delicate wires, or optic fibers through the flexible wrist joint of the instrument. A force sensor apparatus may be manufactured, tested, and calibrated as a separate modular component and brought together with other components in the conventional instrument assembly process. The force sensor apparatus may also be manufactured as an integrated part of the instrument shaft. In addition, it is possible to choose a material for the sensor structural member different from the material of the instrument shaft whose design considerations may compromise the mechanical and/or thermal properties required for the sensor.

In another aspect, a polarization and temperature insensitive surgical instrument force transducer with at least one fiber Bragg grating strain gauge simultaneously mitigates or eliminates: (1) effects of varying light polarization on the output of the strain gauge; (2) temperature sensitivity; and (3) calibration drift.

More specifically, a force sensor apparatus, mounted in the surgical instrument includes the force transducer. The force transducer includes a transducer body having a coefficient of thermal expansion, and at least one optic fiber, fixedly attached to the transducer body. The optic fiber includes a Bragg grating and has a coefficient of thermal expansion matched to the coefficient of thermal expansion of the transducer body. The matching of the coefficients of thermal expansion mitigates polarization sensitivity and calibration drift effects on the force transducer.

In one aspect, the transducer body comprises a metal transducer body, such as a metal alloy transducer body. Suitable metal alloys include, but are not limited to, aluminum alloys, stainless steel alloys, maraging steel alloys, and titanium alloys. In another aspect, the at least one optic fiber comprises an optic fiber having a negative thermo-optic coefficient, largely mitigating the effect of transducer body thermal expansion on fiber Bragg grating strain gauge output. Suitable optic fibers include, but are not limited to, phosphate glass optic fiber, fluoride optic fiber, and oxy-fluoride optic fiber.

In still another aspect, the optic fiber is fixedly attached to the transducer body by an adhesive. The adhesive has a coefficient of thermal expansion matched to the coefficient of thermal expansion of the optic fiber and to the coefficient of thermal expansion of the transducer body.

A method for reducing temperature and polarization effects for an optic fiber Bragg grating strain gauge based robotic surgical instrument force transducer includes:
- selecting a metal transducer body, for the force transducer, having a coefficient of thermal expansion;
- selecting an optic fiber including a fiber Bragg grating for said force transducer, said optic fiber having a coefficient of thermal expansion matched to said coefficient of thermal expansion of said metal transducer body to mitigate polarization effects and calibration drift effects on said force transducer; and
- fixedly attaching the optic fiber including the Bragg grating to the metal transducer body using an adhesive with a coefficient of thermal expansion matching the fiber and transducer body.

In another aspect of the method, the optic fiber is an optic fiber having a negative thermo-optic coefficient, largely mitigating the effect of transducer body thermal expansion on fiber Bragg grating strain gauge output. Suitable optic fibers include, but are not limited to, phosphate glass optic fiber, fluoride optic fiber, and oxy-fluoride optic fiber.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 5C1 illustrates a magnified section labeled 5C1 in FIG. 5C.

FIG. 6C illustrates an end view of the force sensor apparatus of FIGS. 6A and 6B including radial ribs positioned in non-uniform angles, and FIG. 6C1 illustrates a magnified section labeled 6C1 in FIG. 6C, in accordance with another embodiment of the present invention.

FIG. 7B1 illustrates a magnified section labeled 7B1 in FIG. 7B, in accordance with another embodiment of the present invention.

Figure 1A:
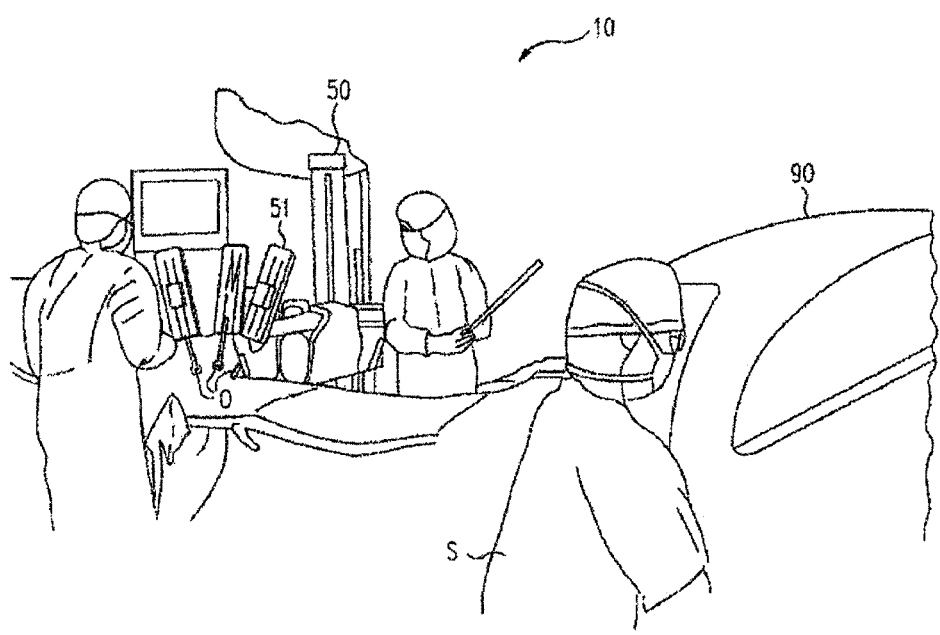
FIG. 1A is a perspective view of a robotic surgical system in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system, apparatus, and method for sensing forces applied to tissue while performing robotically-assisted surgical procedures on a patient, particularly including open surgical procedures, neurosurgical procedures, and minimally invasive procedures, such as laparoscopy, arthroscopy, thoracoscopy, and the like. The apparatus and method of the present invention are particularly useful as part of a telerobotic surgical system that allows the surgeon to manipulate the surgical instruments through a servomechanism from a location remote from the patient. To that end, the combined manipulator apparatus or slave and surgical instrument of the present invention will usually be driven by a master having the same degrees of freedom (e.g., 3 degrees of freedom for position and 3 degrees of freedom for orientation plus grip) to form a telepresence system with force reflection or other scalar force magnitude display. A description of a suitable slave-master system can be found in U.S. Pat. No. 6,574,355, the complete disclosure of which is incorporated herein by reference for all purposes.

Figure 1B:
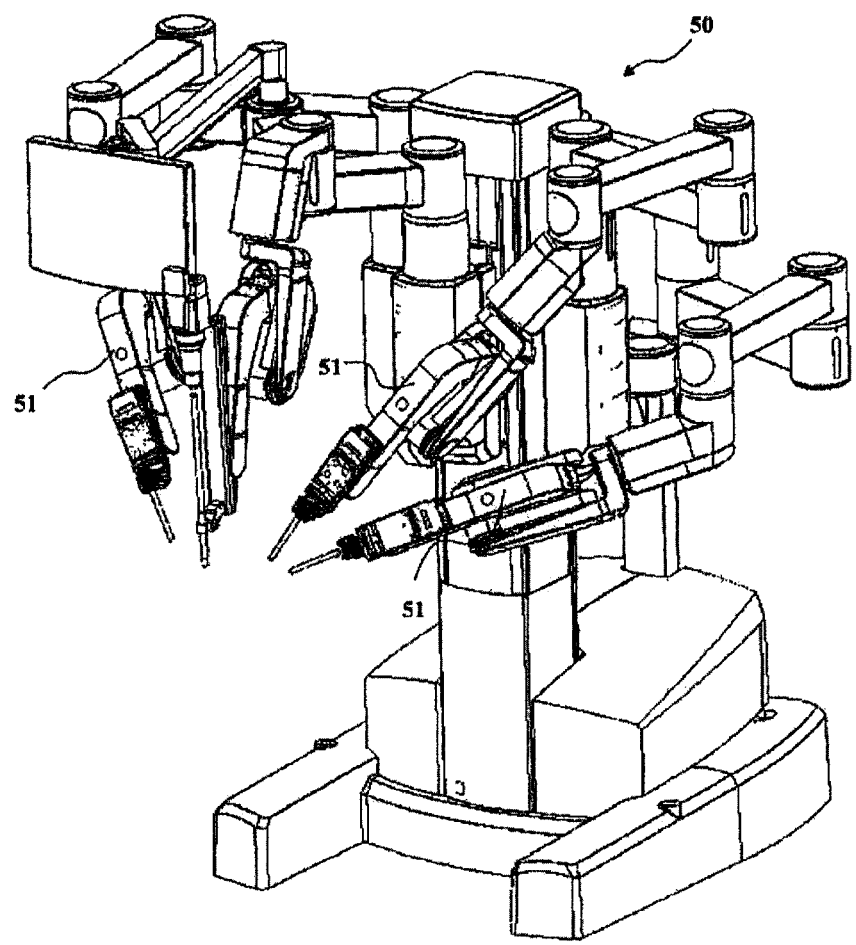
FIG. 1B is a perspective view of a robotic surgical arm cart system of the robotic surgical system in FIG. 1A in accordance with an embodiment of the present invention.
Figure 1C:
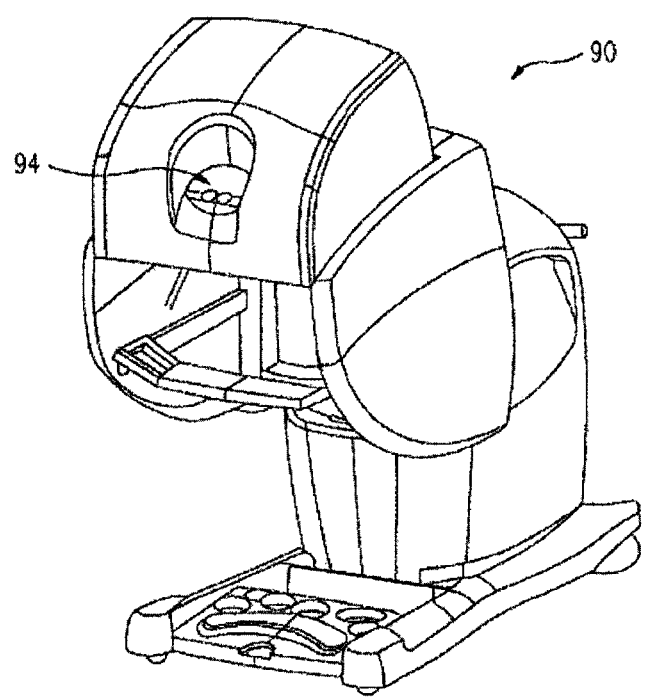
FIG. 1C is a front perspective view of a master console of the robotic surgical system in FIG. 1A in accordance with an embodiment of the present invention.

Referring to the drawings in detail, wherein like numerals indicate like elements, a robotic surgical system 10 is illustrated according to an embodiment of the present invention. As shown in FIGS. 1A through 1C, robotic system 10 generally includes one or more surgical manipulator assemblies 51 mounted to or near an operating table O and a master control assembly located at a surgeon's console 90 for allowing the surgeon S to view the surgical site and to control the manipulator assemblies 51. The system 10 will also include one or more viewing scope assemblies and a plurality of surgical instrument assemblies 54 (FIG. 2) adapted for being removably coupled to the manipulator assemblies 51 (discussed in more detail below). Robotic system 10 includes at least two manipulator assemblies 51 and preferably at least three manipulator assemblies 51. The exact number of manipulator assemblies 51 will depend on the surgical procedure and the space constraints within the operating room among other factors. As discussed in detail below, one of the assemblies 51 will typically operate a viewing scope assembly (e.g., in endoscopic procedures) for viewing the surgical site, while the other manipulator assemblies 51 operate surgical instruments 54 for performing various procedures on the patient.

The control assembly may be located at a surgeon's console 90 which is usually located in the same room as operating table O so that the surgeon may speak to his/her assistant(s) and directly monitor the operating procedure. However, it should be understood that the surgeon S can be located in a different room or a completely different building from the patient. The master control assembly generally includes a support, a monitor for displaying an image of the surgical site to the surgeon S, and one or more master(s) for controlling manipulator assemblies 51. Master(s) may include a variety of input devices, such as hand-held wrist gimbals, joysticks, gloves, trigger-guns, hand-operated controllers, voice recognition devices, or the like. Preferably, master(s) will be provided with the same degrees of freedom as the combined manipulator 51 and surgical instrument assemblies 54. In conjunction with the endoscopic view, this provides the surgeon with telepresence, the perception that the surgeon is immediately adjacent to and immersed in the surgical site, and intuitiveness, the perception that the master(s) are integral with the instruments 54 so that the surgeon has a strong sense of directly and intuitively controlling instruments 54 as if they are part of or held in his/her hands. Position, force, and tactile feedback sensors (not shown) may also be employed on instrument assemblies 54 to transmit position, force, and tactile sensations from the surgical instrument back to the surgeon's hands, ears, or eyes as he/she operates the telerobotic system. One suitable system and method for providing telepresence to the operator is described in U.S. Pat. No. 6,574,355, which has previously been incorporated herein by reference.

The monitor 94 (FIG. 1C) will be suitably coupled to the viewing scope assembly such that an image of the surgical site is provided adjacent the surgeon's hands on the surgeon console. Preferably, monitor 94 will display an image that is oriented so that the surgeon feels that he or she is actually looking directly down onto the operating site. To that end, an image of the surgical instruments 54 appears to be located substantially where the operator's hands are located. In addition, the real-time image is a stereo image such that the operator can manipulate the end effector via the hand control as if viewing the workspace in substantially true presence. The image simulates the viewpoint or orientation of an operator who is physically manipulating the surgical instruments 54.

A servo control is provided for transferring the mechanical motion of masters to manipulator assemblies 51. The servo control may be separate from, or integral with, manipulator assemblies 51. The servo control will usually provide force and torque feedback from the surgical instruments 51 to the hand-operated masters. In addition, the servo control may include a safety monitoring controller (not shown) to safely halt system operation, or at least inhibit all robot motion, in response to recognized undesirable conditions (e.g., exertion of excessive force on the patient, mismatched encoder readings, etc.). The servo control preferably has a servo bandwidth with a 3 dB cut off frequency of at least 10 Hz so that the system can quickly and accurately respond to the rapid hand motions used by the surgeon and yet to filter out undesirable surgeon hand tremors. To operate effectively with this system, manipulator assemblies 51 have a relatively low inertia, and the drive motors have relatively low ratio gear or pulley couplings. Any suitable conventional or specialized servo control may be used in the practice of the present invention, with those incorporating force and torque feedback being particularly preferred for telepresence operation of the system.

Figure 2:
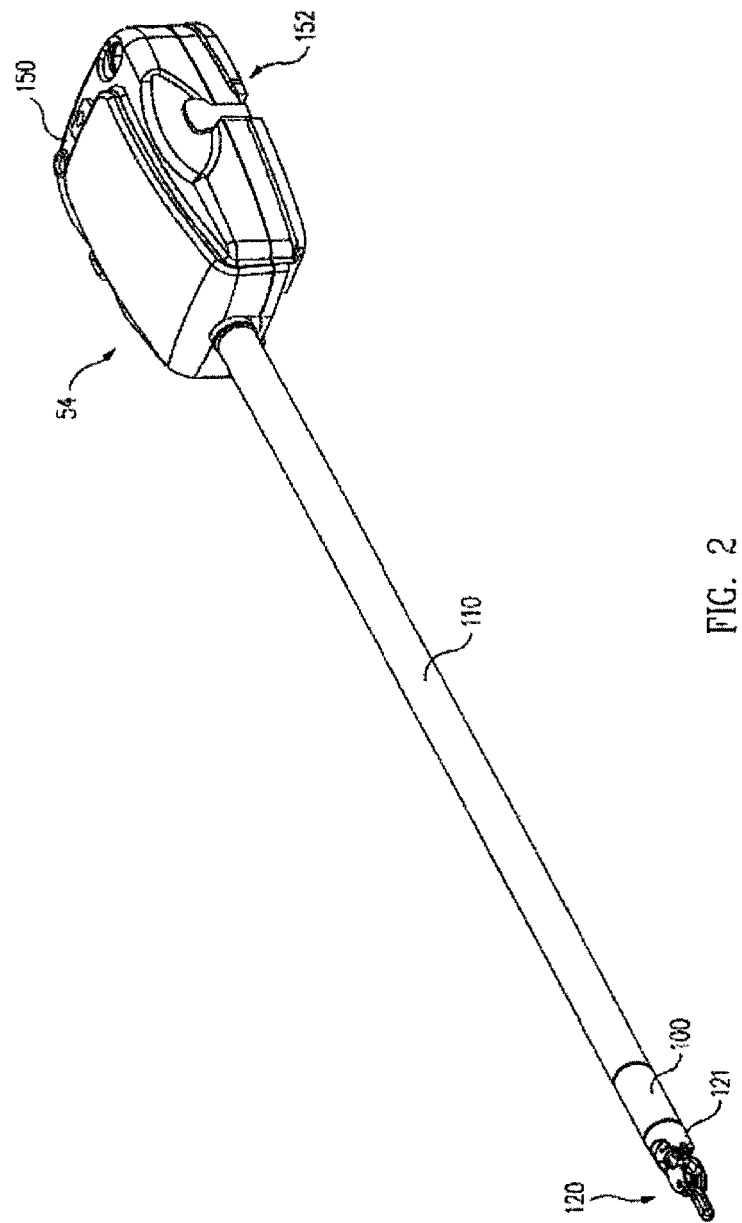
FIG. 2 is a perspective view of a surgical instrument including a force sensor apparatus operably coupled proximal (or inboard) to a wrist joint in accordance with an embodiment of the present invention.

Referring to FIG. 2, a perspective view is shown of a surgical instrument 54 including a force sensor apparatus 100 operably coupled to a distal end of a rigid shaft 110 and proximal to a wrist joint 121 in accordance with an embodiment of the present invention. An end portion 120, such as a surgical end effector, is coupled to force sensor apparatus 100 via the wrist joint 121. A housing 150 is operably coupled to a proximal end of the rigid shaft 110 and includes an interface 152 which mechanically and electrically couples instrument 54 to the manipulator 51.

Figure 3A:
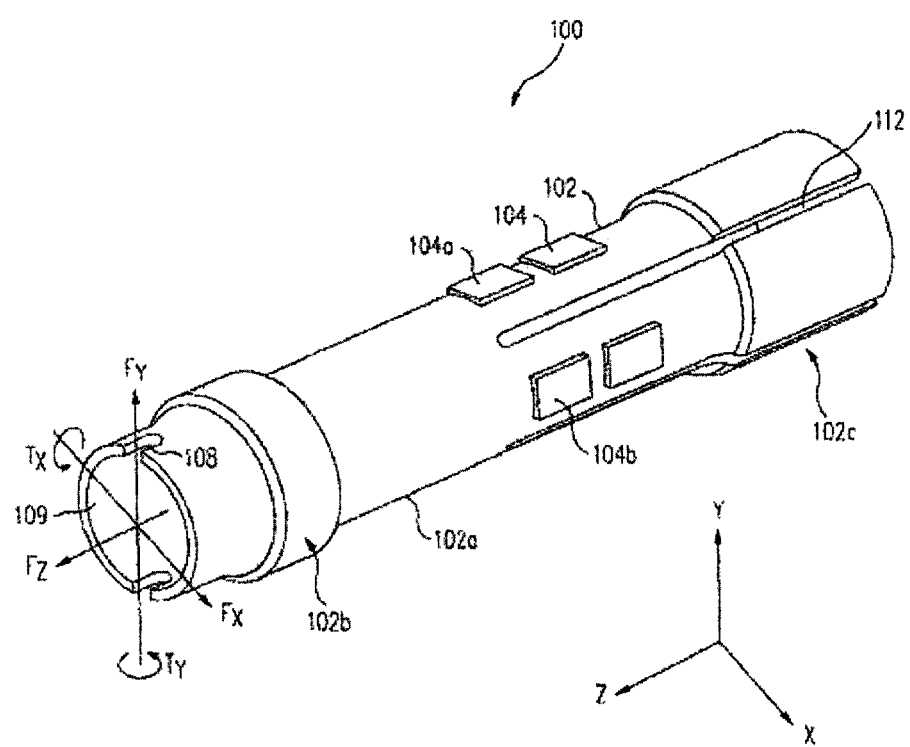
FIG. 3A is a perspective view of a force sensor apparatus.
Figure 3B:
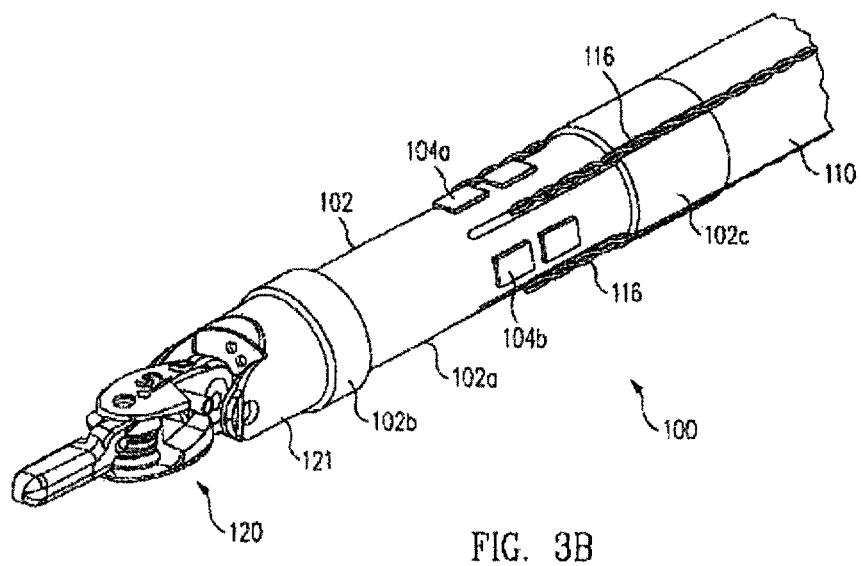
FIG. 3B illustrates the force sensor of FIG. 3A operably coupled to a shaft and end portion of a surgical instrument.
Figure 3C:
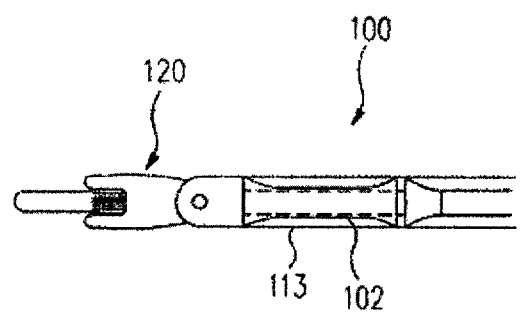
FIG. 3C illustrates the force sensor of FIG. 3A with a protective cover over a portion of the force sensor.

Referring now to FIGS. 3A-3C in conjunction with FIGS. 1A-1C and 2, an improved apparatus, system, and method for sensing and feedback of forces and/or torques to the surgeon will be described. FIG. 3A shows a perspective view of force sensor apparatus 100 including in one embodiment a tube 102 including a number (e.g., 3, 4, 6, or 8) of strain gauges 104 (e.g., 104a and 104b) mounted to a surface of tube 102 and oriented axially (parallel to the lengthwise axis z of the tube). FIG. 3B shows the force sensor apparatus 100 of FIG. 3A operably coupled to a shaft 110 and end portion 120 of a surgical instrument. FIG. 3C shows a cross-section view of force sensor apparatus 100 including a cover or sleeve 113 over tube 102.

Force sensor apparatus 100 is a separately manufacturable module or part adapted for incorporation as part of the shaft 110 of surgical instrument 54 at a prescribed distance from the tip where there may be an articulated wrist with specialized jaws, cutting devices, or other end portion 120. In one example, tube 102 may be made of a sufficiently strong material and may be spool shaped, including end portions 102b, 102c with a depressed portion 102a therebetween that is smaller in diameter than end portions 102b, 102c. Strain gauges 104 may be mounted on the surface of depressed portion 102a. Proximal tube portion 102c operably couples to the shaft 110 of surgical instrument 54 and distal tube portion 102b operably couples to a wrist joint 121. In one example, the diameter of the completed force sensor apparatus matches the diameter of the instrument shaft, thus allowing the entire assembly of the instrument (including the coupled force sensor apparatus) to pass through a cannula or a seal without added friction or snagging.

Force sensor apparatus 100 includes a through passage 109 for end portion actuation cables or rods. End features 108 of end portion 102b insure secure mounting and angular alignment to the main instrument shaft or the wrist/jaw/other end portion sub-assembly of the instrument. Wire leads or optic fibers 116 (e.g., shielded twisted pairs, coax, or fiber) from the strain gauges 104 may be inlaid into grooves 112 in the tube 102 and matching grooves in the shaft 110 of the surgical instrument 54. The wire leads or optic fibers 116 may then be embedded in an adhesive bonding or potting compound such as epoxy.

In one embodiment, as illustrated in FIG. 3C, cover 113 is positioned over and encapsulates the mounted strain gauges 104 and other circuit elements on the surface of the tube 102, thereby providing mechanical and/or electrical protection of the sensors. In one example, cover 113 is a mechanically protective woven sleeve potted on depressed portion 102a and is comprised of a woven resin impregnated fiberglass or metal braid electrical shielding.

As disclosed in U.S. Patent Application Publication No. 2007/0151390 A1 on Jul. 5, 2007 for U.S. patent application Ser. No. 11/537,241, filed Sep. 29, 2006, the contents of which is incorporated by reference, strain gauges 104 may be spaced in a ring at intervals around the circumference of the tube 102 (e.g., 3 gauges at 120 degrees, 4 gauges at 90 degrees, or 4 gauges at 70 degrees and 110 degrees or other pairs of supplementary angles). The signals from the sensors are combined arithmetically in various sums and differences to obtain measures of transverse forces $F_x$ and $F_y$ (FIG. 3A) exerted upon the instrument tip and to reject axial force Fz and the torques Tx and Ty about the two axes perpendicular to the shaft axis (i.e., axes x and y). The measurement of the forces is made independent of the orientation and effective lever arm length of an articulated wrist mechanism 121 at the distal end of the instrument when two axially separated sets or rings of gauges are utilized and their signals are subtracted. Forces exerted against end portion 120 are detected by the force sensing elements via an interrogator 334 (FIG. 5E), which may be operably coupled to the servo control or to a processor 340 (FIG. 5E) for notifying the surgeon of these forces (e.g., via master(s) or a display). It is understood that by adding a second ring of similarly oriented gauges (e.g., two sets of 3 gauges or two sets of 4 gauges) at a different lengthwise axial position on the tube, additional load-induced bending moment information may be obtained, and dependence of the transverse force data Fx, Fy on instrument wrist length, orientation, and resulting jaw distance may be eliminated.

In one example, various strain gauge types may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft for eight gauges.

Both fiber technologies require an interrogator unit 334 that decodes the optically encoded strain information into electrical signals compatible with the computer control hardware 340 or display means of the robotic surgical system. A processor may then be used to calculate forces according to the signals from the strain gauges/sensors.

Additionally, there may be co-mounted unstrained gauges or Poisson strained gauges oriented in the circumferential direction adjacent to each axial gauge and incorporated in the bridge completion circuits to eliminate temperature effects. The strain gauge bridge circuits are completed in a manner to give the best signal for bending loads due to the lateral forces ($F_x$ and $F_y$) exerted on the instrument tip jaws.

For resistive foil or semiconductor strain gauges, active components such as bare die op-amps and passive components such as secondary resistors or capacitors may be attached adjacent to the strain gauges connected by bond wires or thick film circuit traces in the manner of hybrid circuits to amplify, filter, and/or modulate the gauge output signals to reject noise sources. Such components are not needed for fiber optic gauges.

Housing 150 operably interfaces with a robotic manipulator arm 51, in one embodiment via a sterile adaptor interface 152 (FIG. 2). Applicable housings, sterile adaptor interfaces, and manipulator arms are disclosed in U.S. Patent Application Publication No. 2006/0161138 A1 on Jul. 20, 2006 for U.S. patent application Ser. No. 11/314,040 filed on Dec. 20, 2005, and U.S. Patent Application Publication No. 2007/0137371 A1 on Jun. 21, 2007 for U.S. application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 120 has a range of motion that includes pitch and yaw motion about the x- and y-axes and rotation about the z-axis (axes shown in FIG. 3A). These motions as well as actuation of an end effector are provided via cables in housing 150 and cables and/or rods running through shaft 110 and into housing 150 that transfer motion from the manipulator arm 51. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be improved in accordance with the present invention, including but not limited to tools with and without end effectors, such as jaws, scissors, graspers, needle holders, micro-dissectors, staple appliers, tackers, suction irrigation tools, clip appliers, cutting blades, irrigators, catheters, and suction orifices. Alternatively, the surgical instrument may comprise an electrosurgical probe for ablating, resecting, cutting or coagulating tissue. Such surgical instruments are available from Intuitive Surgical, Inc. of Sunnyvale, Calif.

For the methods and apparatus mentioned above, it may be advantageous to use a calibration process in which combinations of forces and torques are applied to the instrument tip serially or in simultaneous combinations while correction factors and offsets are determined. The correction factors and offsets may then be applied to the theoretical equations for combining the gauge outputs to obtain $F_x$, $F_y$, and reject $F_z$, $T_x$, and $T_y$. Such a calibration process may be done either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Advantageously, force sensor apparatus 100 is adaptable to the size and shape constraints of various robotic surgical instruments and is suitable for a variety of instruments. Accordingly, end portions 102b, 102c may be formed into various applicable shapes and sizes. Furthermore, force sensor apparatus 100 may be manufactured, tested, and calibrated as a separate modular component and brought together with other components in the conventional instrument assembly process. Also, the sensor may be a slip-on module with suitable electrical contacts that mate with contacts on the instrument shaft permitting a higher value sensor to be used with lower cost instruments of limited cycle life. In addition, the sensor structural member 102 may be comprised of an advantageous material, which may be the same or a different material than the instrument shaft 110 whose design considerations may compromise the properties required for the sensor.

Referring now to FIGS. 4A through 4D, a force sensor apparatus 200 is illustrated. The descriptions of substantially similar parts or elements as those described above with respect to FIGS. 3A-3C are applicable in this embodiment with respect to FIGS. 4A-4D, and redundant descriptions may be omitted.

Figure 4A:
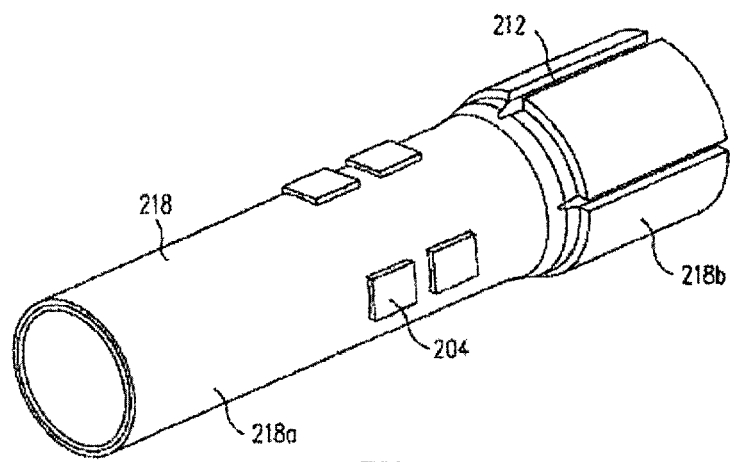
FIG. 4A is a perspective view of an inner tube of another force sensor apparatus.

FIG. 4A is a perspective view of an inner tube 218 of force sensor apparatus 200. Inner tube 218 includes a proximal raised end portion 218b and a depressed portion 218a smaller in diameter than raised end portion 218b. Strain gauges, as described above with respect to FIGS. 3A-3C, may be mounted on the surface of depressed portion 218a. Raised end portion 218b may include grooves 212 for routing of wire leads or optic fibers from strain gauges 204.

Figure 4B:
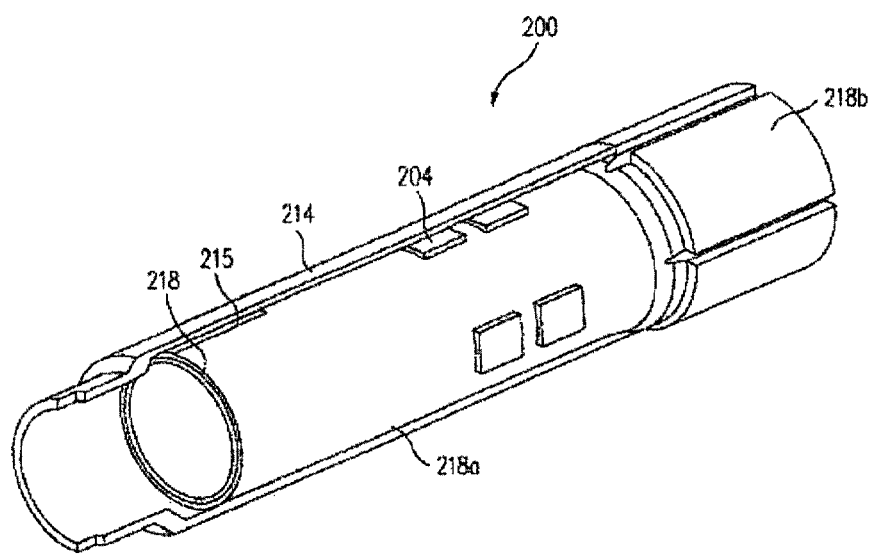
FIG. 4B is a partial cross-sectional view of an outer tube/cover over the inner tube of FIG. 4A of the force sensor apparatus.
Figure 4C:
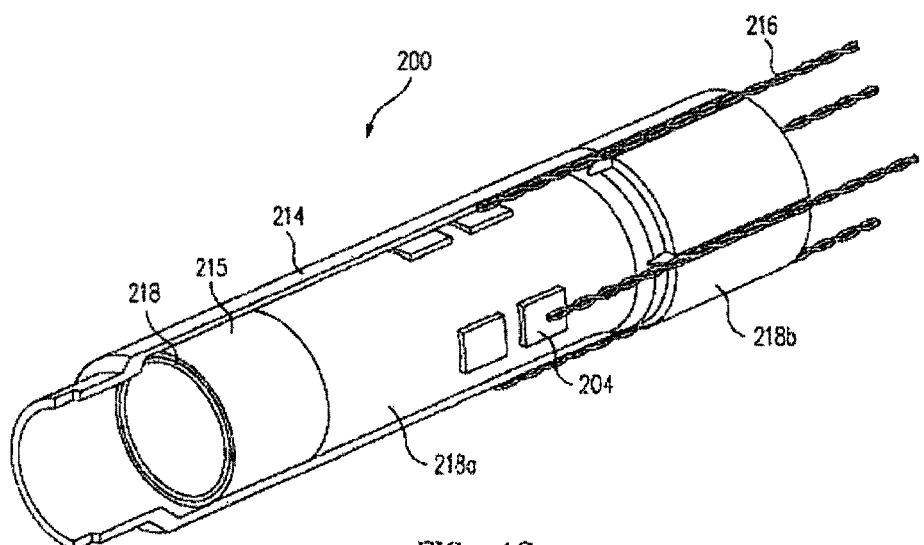
FIG. 4C shows intervening material between the inner and outer tubes of FIG. 4B of the force sensor apparatus and wires or optic fibers operably coupled to the force sensor apparatus.
Figure 4D:
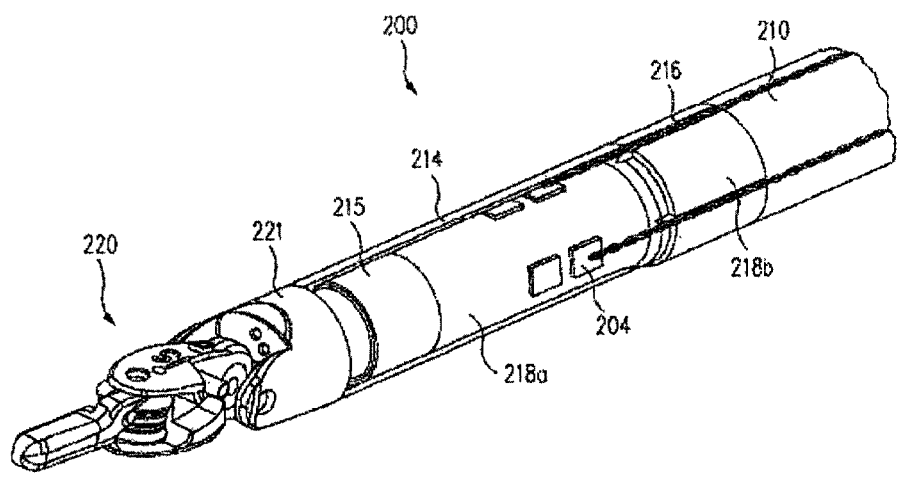
FIG. 4D shows a partial cross-sectional view of the force sensor apparatus of FIG. 4C operably coupled proximal to (or inboard of) a wrist joint of a surgical instrument.

FIG. 4B is a partial cross-sectional view of an outer tube 214 over the inner tube 218. In one example, outer tube 214 can provide mechanical and thermal protection of strain gauges 204 on inner tube 218. FIG. 4C highlights elastomeric material 215 between inner tube 218 and outer tube 214 maintaining concentricity of the tubes. Leads or optic fibers 216 connecting gauges 204 with data acquisition means are inlaid into grooves 212 and may be bonded in place with epoxy or other adhesive. Finally in FIG. 4D wrist 221 and end effector 220 are connected distally to tube 214.

Figure 5A:
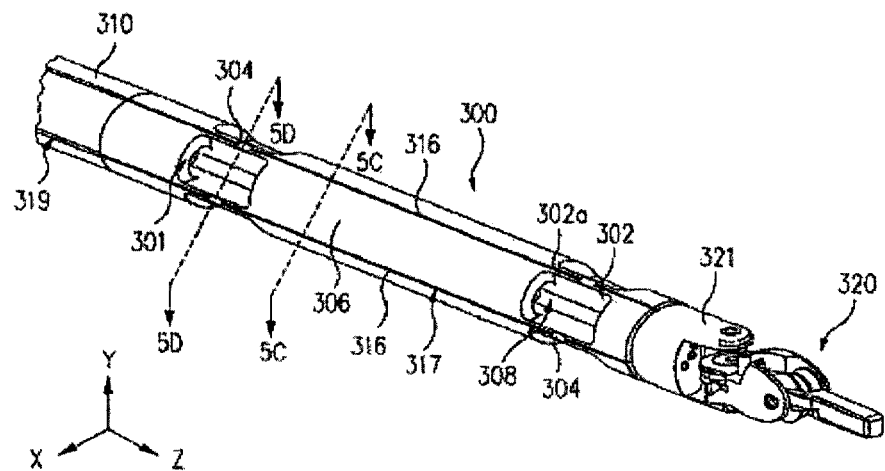
FIG. 5A is a perspective view of a force sensor apparatus in accordance with yet another embodiment of the present invention.
Figure 5B:
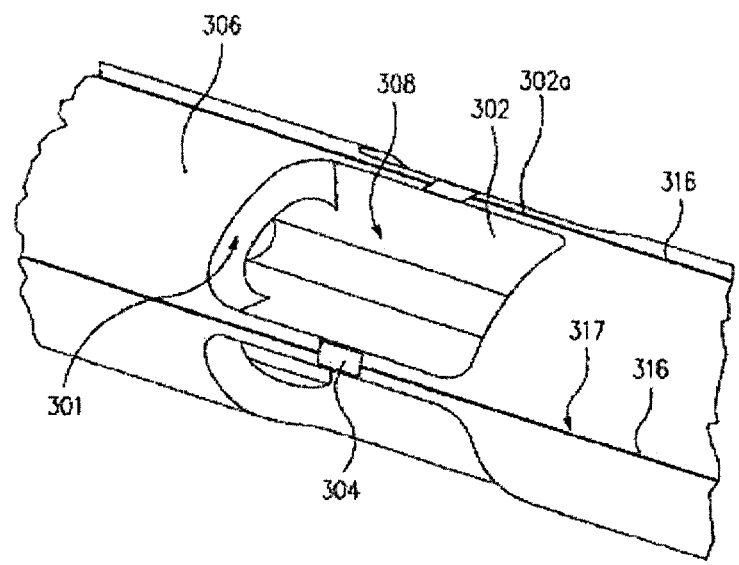
FIG. 5B illustrates an enlarged perspective view of a section of the force sensor apparatus of FIG. 5A.
Figure 5C:
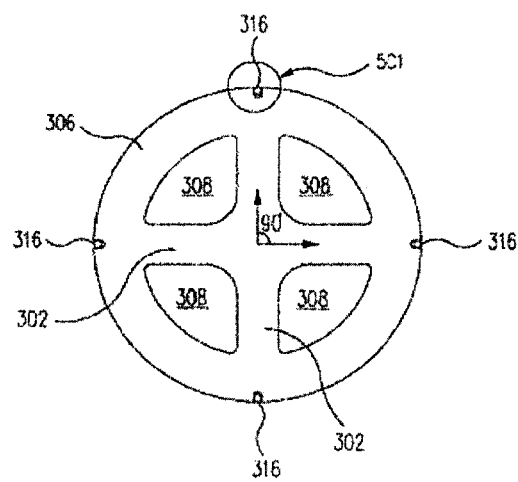
FIG. 5C illustrates a cross-sectional view of the force sensor apparatus of FIG. 5A along line 5C-5C.
Figure 5D:
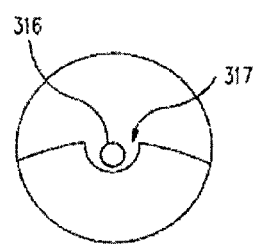
FIG. 5D illustrates a cross-sectional view of the force sensor apparatus of FIG. 5A along line 5D-5D.
Figure 5D:
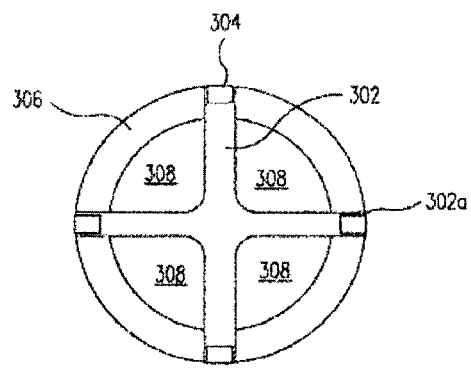
Figure 5E:
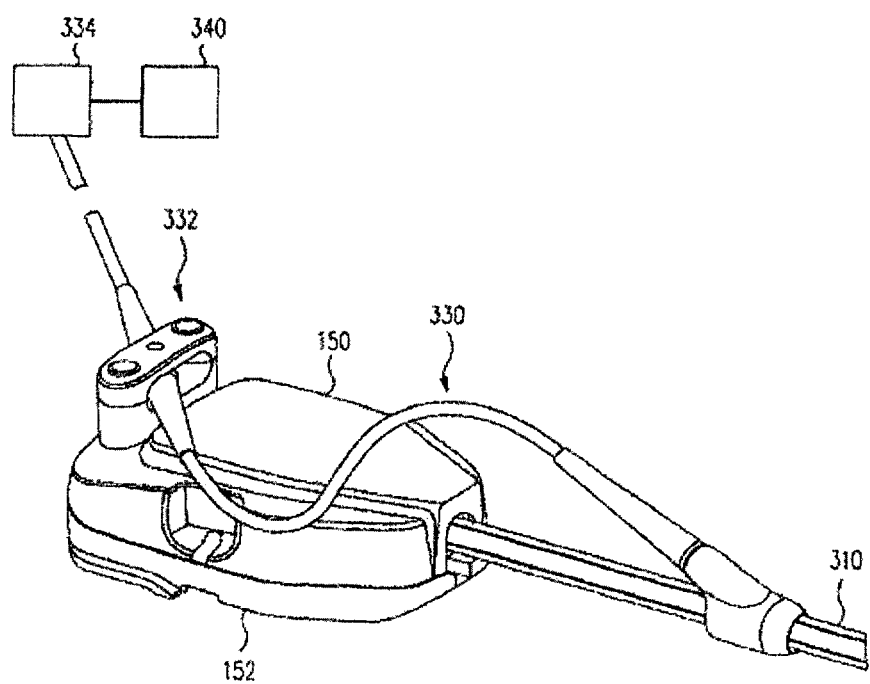
FIG. 5E illustrates a strain relief for strain gauge wires or optic fibers in accordance with an embodiment of the present invention.

Referring now to FIGS. 5A-5E, views of a surgical instrument including another force sensor apparatus 300 is illustrated in accordance with yet another embodiment. An end portion 320, such as a surgical end effector, is coupled to force sensor apparatus 300 via a wrist joint 321. A housing 150 (FIG. 5E) is operably coupled to a proximal end of a rigid shaft 310, the housing 150 further including an interface 152 which mechanically and electrically couples the instrument to the manipulator 51 (FIG. 1B). FIG. 5B is an enlarged perspective view of an aperture and rib section of the force sensor apparatus of FIG. 5A. FIGS. 5C and 5D are cross-sectional views of the force sensor apparatus of FIG. 5A along lines 5C-5C and 5D-SD, respectively, and FIG. 5C1 illustrates a magnified section labeled 5C1 in FIG. 5C. FIG. 5E illustrates an example proximal portion of the surgical instrument including the housing and operably coupling of the instrument to an interrogator 334 and processor 340. The descriptions of substantially similar parts or elements as those described above with respect to FIGS. 1-4 are applicable in this embodiment with respect to FIGS. 5A-5E, although redundant descriptions may be omitted.

Returning to FIG. 5A, force sensor apparatus 300 includes a generally annular tube 306 operably coupled to a distal end of rigid shaft 310 and proximal to wrist joint 321 in accordance with an embodiment. In one embodiment, tube 306 includes a number of rectangular-shaped apertures 301 cut from tube 306 and a plurality of radial ribs 302 forming through passages 308 for passage of actuation cables, wires, tubes, rods, cautery wires and/or flushing fluids. Ribs 302 run along and radiate from the z-axis centerline of tube 306, and a number (e.g., 3, 4, 6, or 8) of strain gauges 304 are oriented parallel to the lengthwise z-axis of the tube and mounted to an outer rib surface 302a. The strain gauges may be inlaid into grooves or a depressed area 317 on the outer rib surface 302a in one example.

In the embodiment illustrated in FIGS. 5A-5D, force sensor apparatus 300 includes two sets of four apertures 301 cut from the wall of tube 306 at separate axial locations along tube 306. Each of the ribs 302 are separated by 90 degrees measured about the z-axis centerline of tube 306, which forms a cruciform cross-sectional view of the ribs 302, as shown in FIGS. 5C and 5D. Ribs 302 form four through passages 308. Furthermore, ribs 302 may extend along the entire length of tube 306 thereby forming internal through passages 308 along the entire length of tube 306, or ribs 302 may extend along a portion(s) of the length of tube 306, thereby forming internal through passages along a portion or portions of the length of tube 306.

Force sensor apparatus 300 is capable of sensing bending moments due to lateral forces applied to the wrist joint 321 or its specialized end portion 320. Advantageously, apertures 301 and ribs 302 provide for regions of controlled stress and strain when subjected to bending moments, which may be measured by fiber optic strain gauges 304 embedded in grooves 317 along an outer surface of the ribs and sensor body parallel to the lengthwise z-axis of tube 306. Through passages 308 permit cables, wires, tubes, or rigid tendons to pass through the sensor apparatus body to actuate the distal wrist joint(s) and/or control the end portion.

In one example, tube 306 and ribs 302 may be made of a sufficiently strong but elastic material to allow sensing of stress and strain without mechanical failure. Tube 306 and ribs 302 are further comprised of material with a sufficiently low modulus of elasticity to give a sufficient strain signal under an applied load, a sufficiently high strain at yield to give adequate safety margin above the maximum design load, and a sufficiently high thermal diffusivity to promote rapid thermal equilibrium (therefore reducing thermal disturbances to sensor output signals) when subject to localized or asymmetric thermal disturbances from tissue contact or endoscope illumination. In particular, the plurality of radial ribs 302 may be comprised of a high thermal diffusivity material, such as an aluminum alloy (e.g., 6061-T6 aluminum) or a copper alloy (e.g., GlidCop® AL-60) or a silver alloy to reduce the temperature difference between opposing gauges under transient thermal disturbances by providing a direct thermal pathway between opposing gauges.

In one example, tube 306 may be comprised of metal alloys, treated metals, or plated metals, such as of aluminum, copper, or silver, which allow for adequate strain, mechanical failure safety margin, and high thermal diffusivity. In a further example, 6061-T6 aluminum, which is an aluminum alloy that is heat treated and aged, GlidCop® AL-60, which is copper that is dispersion strengthened with ultrafine particles of aluminum oxide, or a dispersion strengthened silver, may be used to form tube 306 and ribs 302. Accordingly, both the plurality of ribs and the tube 302 may be comprised of a high thermal diffusivity material, such as an aluminum alloy (e.g., 6061-T6 aluminum) or a copper alloy (e.g., GlidCop® AL-60) or silver alloy to reduce transient and/or steady-state temperature differences between groups of strain gauges separated along the z-axis.

Advantageously, the present invention allows for a low bending moment of inertia to increase a strain signal to noise signal ratio consistent with a materials choice and rib design meeting the need for high thermal diffusivity and a direct thermal path between opposing strain gauges while also providing passage for actuation cables, wires, tubes, and/or rods.

Wire leads or optic fibers 316 (e.g., shielded twisted pairs, coax, or fiber) coupled to the strain gauges 304 may be inlaid into grooves 317 on tube 306, the outer rib surface 302*a*, and matching grooves 319 in shaft 310 of the surgical instrument. The wire leads or optic fibers 316 may then be embedded in an adhesive bonding or potting compound such as epoxy.

As disclosed in U.S. Patent Application Publication No. 2007/0151390 A1 on Jul. 5, 2007 for U.S. patent application Ser. No. 11/537,241, filed Sep. 29, 2006, the contents of which have been previously incorporated by reference, strain gauges 304 may be spaced in a ring at intervals around the circumference of the tube 306 mounted on ribs 302 (e.g., 3 gauges at 120 degrees, 4 gauges at 90 degrees, 4 gauges at 70 and 110 degrees or other supplementary pairs of angles). The signals from the sensors are combined arithmetically in various sums and differences to obtain measures of the transverse forces $F_x$, $F_y$, and to reject axial forces $F_z$ exerted upon the instrument tip and to reject wrist torques about the two axes perpendicular to the shaft axis (i.e., axes x and y). In accordance with the present invention, the measurement of the transverse forces is made independent of the orientation and effective lever arm length of an articulated wrist mechanism at the distal end of the instrument as well as wrist friction moments and actuator cable tensions when two axially separated sets or rings of gauges are utilized. Forces exerted against end portion 320 are detected by the force sensing elements, which may be operably coupled to the servo control or surgeon display means via an interrogator 334 and to a processor 340 for notifying the surgeon of these forces (e.g., via master(s) or a display means). It is understood that by adding a second ring of similarly oriented gauges (e.g., two sets of 3 gauges or two sets of 4 gauges) at a different position along the z-axis of the tube, additional side load-induced moment information can be obtained, and dependence of the force data on instrument wrist length, orientation, and resulting jaw distance and cable tensions, can be eliminated.

In one example, various strain gauges may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft. Fiber optic gauges may also be desirable because of their immunity to disturbance from cautery and other electromagnetic noise.

A problem with the use of FBG strain gauges in conventional fiber such as SMF-28 is their inherent positive temperature sensitivity, being especially problematic when the FBG strain gauges are mounted to materials with a positive thermal expansion coefficient, which adds to the temperature sensitivity of the FGB strain gauges. Temperature sensitivity limits the accuracy of a force transducer utilizing SMF-28 FBGs and positive thermal expansion coefficient substrate materials, especially under asymmetric transient thermal loads that may occur in surgery.

Intrinsic and extrinsic temperature compensation of FBG strain sensors may be accomplished with additional gratings written in the same or nearby region of the fiber and may include the use of additional fibers, exotic doped fibers spliced together, highly bi-refringent fiber or other means to differentiate thermal responses so that simultaneous equations in strain and temperature with respect to wavelength shift can be solved to obtain the strain independent of the temperature of any single grating. These methods typically require additional interrogator channels or exotic interrogation methods and may result in poorly conditioned pairs of equations.

In another example, the plurality of fiber optic strain gauges 304 may be comprised of a negative thermo-optic coefficient optical fiber material, such as phosphate glass fiber, fluoride glass fiber, oxy-fluoride glass fiber, tellurite glass fiber, or a polymer fiber. The negative thermo-optic coefficient fiber advantageously reduces or eliminates the combined effect of a positive thermo-optic coefficient fiber, such as SMF-28 or other doped fiber, and the positive thermal expansion coefficient of the sensor body material.

Advantageously, the embodiments provide apparatus and methods for improved thermal stability when subjected to temperature changes, such as when entering the patient body from a lower temperature operating room environment, contacting warm living tissue, absorbing incident light from an endoscope illuminator, or other source of thermal disturbance that may occur during surgery. Also, the present invention provides for cost savings, relative ease of manufacture, higher field reliability, and accurate strain measurements.

Both FBG and Fabry-Perot fiber technologies require an interrogator unit, such as interrogator unit 334 (FIG. 5E) that decodes the optically encoded strain information into electrical signals compatible with the computer control hardware of the robotic surgical system. A processor 340 (FIG. 5E) operably coupled to the interrogator unit 334 may then be used to calculate forces according to the signals from the strain gauges/sensors.

For resistive foil or semiconductor strain gauges, active components such as bare die op-amps and passive components such as secondary resistors or capacitors may be attached adjacent to the strain gauges connected by bond wires or thick film circuit traces in the manner of hybrid circuits to amplify, filter, and/or modulate the gauge output signals to reject noise sources. Such components are not needed for fiber optic gauges.

In accordance with an embodiment, force sensor apparatus 300 is a separately manufactured module or part adapted for incorporation as part of the shaft 310 of a laparoscopic surgical instrument at a prescribed distance from the tip where there may be an articulated wrist with specialized jaws, cutting devices, or other end portion 320. A proximal portion of tube 306 operably couples to the shaft 310 of the surgical instrument and a distal portion of tube 306 operably couples to wrist joint 321. In one example, the diameter of the completed force sensor apparatus matches the diameter of the instrument shaft, thus allowing the entire assembly of the instrument (including the coupled force sensor apparatus) to pass through a cannula or a seal without added friction or snagging. In other embodiments, the surgical instrument may be manufactured with a force sensor portion integrated as a part of shaft 310 (i.e., force sensor apparatus 300 is not separable from the shaft).

Similar to the embodiments described above, the surgical instrument to which force sensor apparatus 300 couples may also include a service loop 330 (FIG. 5E) of conductive traces or optic fibers at the proximal end of the instrument shaft 310 and a cable swivel mechanism 332 permitting the substantially free rotation of the instrument shaft while conducting the input gauge excitation power or light and electrical or optical output gauge signals to the interrogator unit 334. Other routings of the optic fibers can be used. For example, the optic fibers can be routed along the internal centerline of the tube back to the rear housing as described in copending and commonly assigned U.S. patent application Ser. No. 12/415,795, entitled "Optic Fiber Connection For a Force Sensing Instrument," of Stephen J. Blumenkranz et al. filed on Mar. 31, 2009, and U.S. patent application Ser. No. 12/468,618 entitled "Cleaning of a Surgical Instrument Force Sensor," of Stephen J. Blumenkranz filed on May 19, 2009, each of which is incorporated herein by reference in its entirety.

Similar to the embodiments described above, the housing 150 operably interfaces with a robotic manipulator arm, in one embodiment via a sterile adaptor interface. Applicable housings, sterile adaptor interfaces, and manipulator arms are disclosed in U.S. Patent Application Publication No. 2006/0161138 A1 on Jul. 20, 2006 for U.S. patent application Ser. No. 11/314,040 filed on Dec. 20, 2005, and U.S. Patent Application Publication No. 2007/0137371 A1 on Jun. 21, 2007 for U.S. application Ser. No. 11/613,800 filed on Dec. 20, 2006 U.S., the full disclosures of which were previously incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 320 has a range of motion that includes pitch and yaw motion about the x- and y-axes and rotation about the z-axis. These motions as well as actuation of an end effector are provided via cables in the housing 150 and cables and/or rods running through the shaft and into the housing that transfer motion from the manipulator arm. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be improved in accordance with the present invention, including but not limited to tools with and without end effectors, such as jaws, scissors, graspers, needle holders, micro-dissectors, staple appliers, tackers, suction irrigation tools, clip appliers, cutting blades, hooks, sealers, lasers, irrigators, catheters, and suction orifices. Alternatively, the surgical instrument may comprise an electrosurgical probe for ablating, resecting, cutting or coagulating tissue. Such surgical instruments are manufactured by Intuitive Surgical, Inc. of Sunnyvale, Calif.

For the sensing methods and apparatus mentioned above, it may be advantageous to use a calibration process in which combinations of forces and torques are applied to the instrument tip serially, simultaneously, or in combinations while correction factors and offsets are determined to apply to the theoretical equations for combining the gauge outputs to obtain $F_x$, $F_y$, and reject $F_z$, $T_x$, and $T_y$. This calibration may be done either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Advantageously, force sensor apparatus 300 is adaptable to the size and shape constraints of robotic endoscopic surgical instruments and is suitable for a variety of instruments. Furthermore, force sensor apparatus 300 may be manufactured, tested, and calibrated as a separate modular component and brought together with other components in the conventional instrument assembly process or as an integrated part of the instrument shaft 310. Also, the sensor may be a slip-on module permitting a higher value sensor to be used with lower cost instruments of limited cycle life.

The present invention is not limited to rib orientation or a certain number of ribs, sets of ribs, strain gauges, or tube apertures, and FIGS. 6A-6C1, 7A-7B1, 8, and 9A-9C illustrate force sensor apparatus in accordance with other embodiments. The descriptions of substantially similar parts or elements as those described above with respect to FIGS. 5A-5E are applicable in these embodiments although redundant descriptions may be omitted.

Figure 6A:
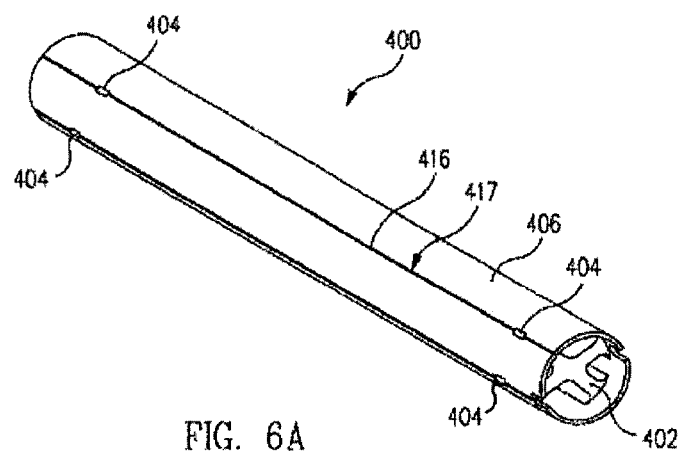
FIGS. 6A and 6B illustrate perspective views of another force sensor apparatus and an enlarged view of a portion of the force sensor apparatus in accordance with another embodiment of the present invention.
Figure 6B:
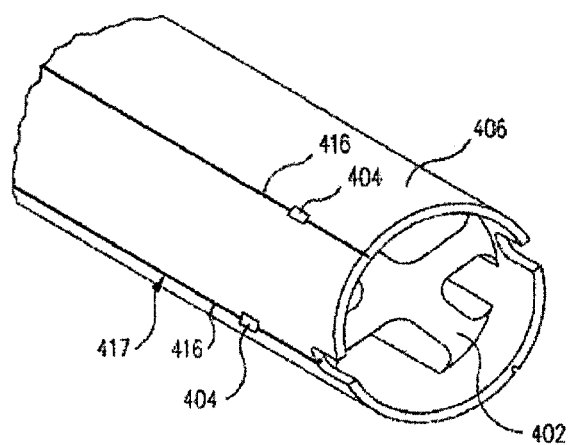

Referring now to FIGS. 6A-6C1, a force sensor apparatus 400 is illustrated, the force sensor apparatus 400 including four ribs 402 in diametrically opposite pairs at skewed supplementary angles (e.g., 70 degrees and 110 degrees) about a z-axis centerline of a tube 406. Ribs 402 extend radially within tube 406 from the z-axis centerline of the tube providing four through passages 408a and 408b for passage of actuation cables, wires, tubes, rods, cautery wires and/or flushing fluids. Advantageously, a larger through passage 408a utilizing skewed angles allows for easier passage of cables, wires, tubes, and/or rods through tube 406 (e.g., three hypodermic tubes may be passed per 110 degree channel). In this embodiment, as can be seen in FIG. 6A, tube 406 does not include apertures through the wall of tube 406. However, the combined stiffness of tube 406 and ribs 402 still allow for a strong strain signal to noise signal ratio consistent with a materials choice and rib design meeting the need for high thermal diffusivity and a direct thermal path between opposing strain gauges while also providing passage for actuation cables, wires, tubes, and/or rods.

Similar to the embodiments disclosed above, a number of strain gauges 404 are oriented parallel to the lengthwise z-axis of the tube and mounted to an outer rib surface 402a. The strain gauges may be inlaid into grooves or a depressed area 417 on the outer rib surface 402a in one example. Wire leads or optic fibers 416 (e.g., shielded twisted pairs, coax, or fiber) coupled to the strain gauges 404 may be inlaid into grooves 417 on the outer rib surface 402a of tube 406. The wire leads or optic fibers 416 may then be embedded in an adhesive bonding or potting compound such as epoxy.

Referring now in particular to FIGS. 6C and 6C1, an end view of force sensor apparatus 400 and a magnified section labeled 6C1 in FIG. 6C are respectively illustrated. A thermal shielding over the strain gauges may be provided in accordance with another embodiment. In one example, a thermal shunt shell 452 is provided over tube 406 with an insulating fluid (gas or liquid) filled or evacuated gap 450 being provided between the outer surface of tube 406 and the inner surface of thermal shunt shell 452. Thermal shunt shell 452 may be comprised of a high thermal diffusivity material, such as an aluminum alloy (e.g., 6061-T6 aluminum) or a copper alloy (e.g., GlidCop® AL-60) or a silver alloy. Optionally, a light reflective surface or coating 453 may be provided over thermal shunt shell 452, which may deflect light and reduce localized heating of the force sensor apparatus, for example from endoscope illumination. An insulating coating 454 may also be provided over thermal shunt shell 452, the insulating coating 454 being comprised of a substantially transparent plastic shrink polymer in one example. Advantageously, the thermal shielding over the sensor tube 406 and the strain gauges 404 as described above allows for more uniform heat/thermal diffusion among the gauges, being particularly advantageous for mitigating asymmetric thermal loads upon the instrument. The thermal shielding described above is applicable for various embodiments.

Figure 7A:
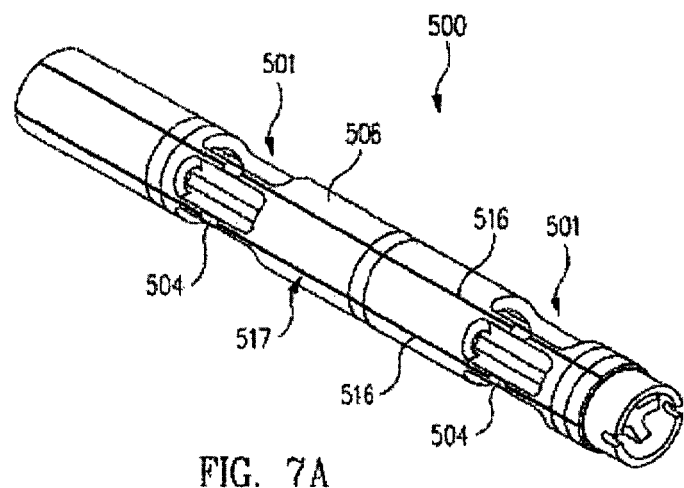
FIGS. 7A and 7B illustrate a perspective view and an end view of another force sensor apparatus including radial ribs positioned in non-uniform supplementary angles and exposed by apertures on the tube surface.
Figure 7B:
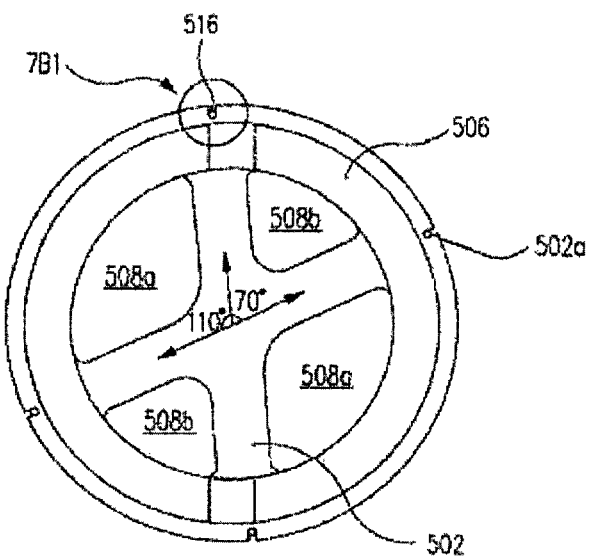

Referring now to FIGS. 7A thru 7B1, a force sensor apparatus 500 is illustrated, the force sensor apparatus 500 including four ribs 502 paired at skewed angles (e.g., 70 degrees and 110 degrees) about a z-axis centerline of a tube 506. Ribs 502 extend radially within tube 506 from the z-axis centerline of the tube providing four through passages 508a and 508b for passage of actuation cables, wires, tubes, rods cautery wires and/or flushing fluids. Advantageously, a larger through passage 508a utilizing skewed angles allows for easier passage of cables, wires, tubes, and/or rods through tube 506 (e.g., three hypodermic tubes may be passed per 110 degree channel). In this embodiment, as can be seen in FIG. 7A, tube 506 include apertures 501 provided through the wall of tube 506. The reduced stiffness of exposed ribs 502 allow for a strong strain signal to noise signal ratio consistent with a materials choice and rib design meeting the need for high thermal diffusivity and a direct thermal path between opposing strain gauges while also providing passage for actuation cables, wires, tubes, rods, and the like.

Similar to the embodiments disclosed above, a number of strain gauges 504 are oriented parallel to the lengthwise z-axis of the tube and mounted to an outer rib surface 502a. The strain gauges may be inlaid into grooves or a depressed area 517 on the outer rib surface 502a in one example. Wire leads or optic fibers 516 (e.g., shielded twisted pairs, coax, or fiber) coupled to the strain gauges 504 may be inlaid into grooves 517 on tube 506, the outer rib surface 502a, and matching grooves 517 in a shaft of the surgical instrument. The wire leads or optic fibers 516 in grooves 517 may then be embedded in an adhesive bonding or potting compound such as epoxy.

Figure 8:
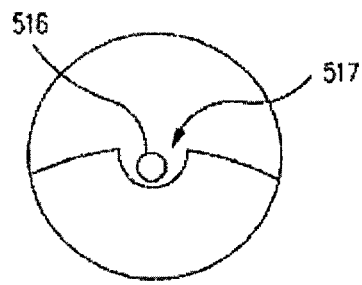
FIG. 8 illustrates an end view of another force sensor apparatus including three radial ribs in accordance with another embodiment of the present invention.
Figure 8:
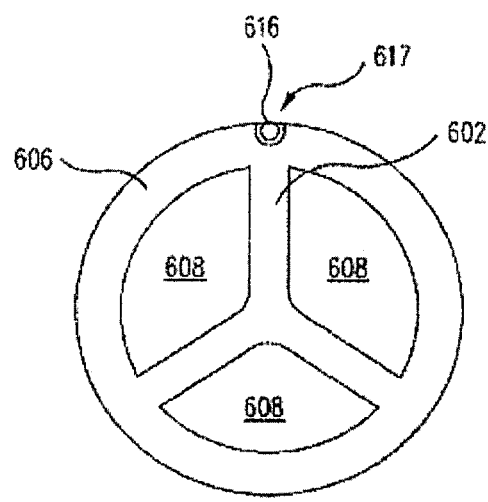

FIG. 8 illustrates a cross-sectional view of another force sensor apparatus which includes three ribs 602 separated by 120 degrees about a z-axis centerline of the force sensor apparatus tube 606. Ribs 602 provide three through passages 608. Wire leads or optic fibers 616 (e.g., shielded twisted pairs, coax, or fiber) coupled to strain gauges may be inlaid into grooves 617 on an instrument tube, an outer rib surface, and matching grooves in a shaft of the surgical instrument.

Figure 9A:
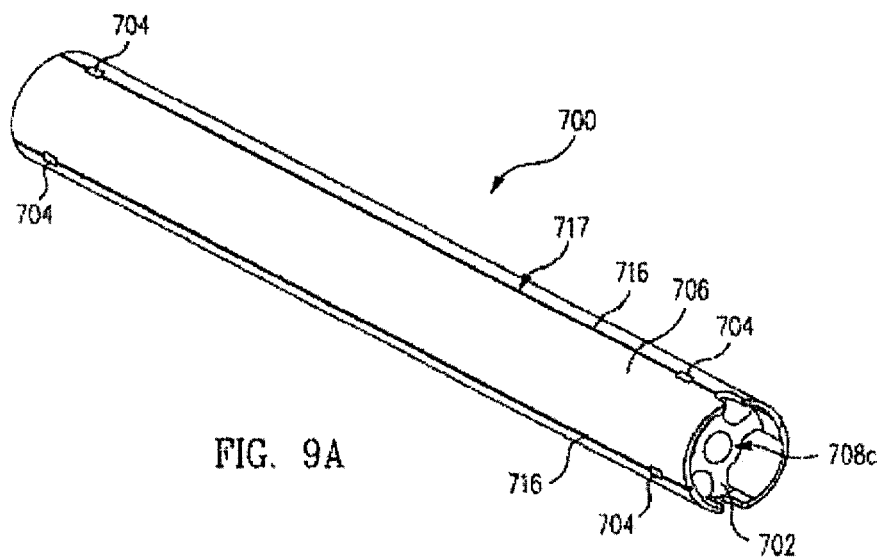
FIGS. 9A and 9B illustrate perspective views of another force sensor apparatus and an enlarged section of the force sensor apparatus, respectively, in accordance with another embodiment of the present invention.
Figure 9B:
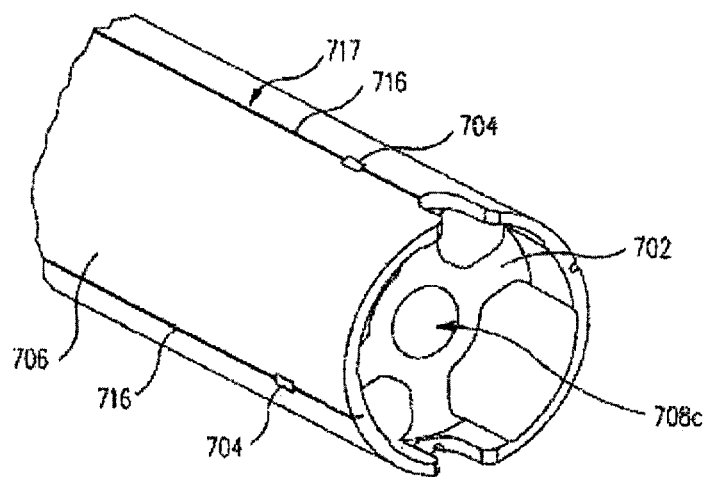
Figure 9C:
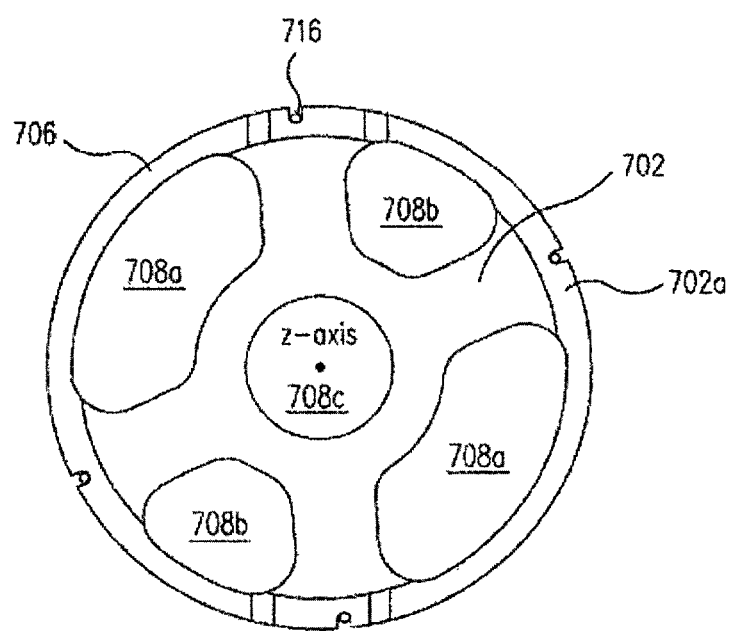
FIG. 9C illustrates an end view of the force sensor apparatus of FIGS. 9A and 9B including radial ribs positioned in non-uniform supplementary angles and a central through passage in accordance with another embodiment of the present invention.

Referring now to FIGS. 9A-9C, a force sensor apparatus 700 is illustrated, the force sensor apparatus 700 including four ribs 702 paired at skewed angles (e.g., 70 degrees and 110 degrees) about a z-axis centerline of a tube 706. Ribs 702 extend radially within tube 706 from the z-axis centerline of the tube providing through passages 708a and 708b. In this embodiment, force sensor apparatus 700 also includes a central through passage 708c along a lengthwise axis of tube 706 in accordance with another embodiment. The through passages may be used for passage of actuation cables, wires, tubes, rods, and/or fluids. In this embodiment, as can be seen in FIG. 9A, tube 706 does not include apertures through the wall of the tube but apertures exposing portions of the interior ribs are within the scope of the present invention. Furthermore, the combined stiffness of tube 706 and ribs 702 still allow for a strong strain signal to noise signal ratio consistent with a materials choice and rib design meeting the need for high thermal diffusivity and a thermal path between opposing strain gauges while also providing passage for actuation cables, wires, tubes, rods, and/or fluids.

Similar to the embodiments disclosed above, a number of strain gauges 704 are oriented parallel to the lengthwise z-axis of the tube and mounted to an outer rib surface 702a. The strain gauges may be inlaid into grooves or a depressed area 717 on the outer rib surface 702a in one example. Wire leads or optic fibers 716 (e.g., shielded twisted pairs, coax, or fiber) coupled to the strain gauges 704 may be inlaid into grooves 717 on the outer rib surface 702a of tube 706. The wire leads or optic fibers 716 may then be embedded in an adhesive bonding or potting compound such as epoxy.

Figure 10:
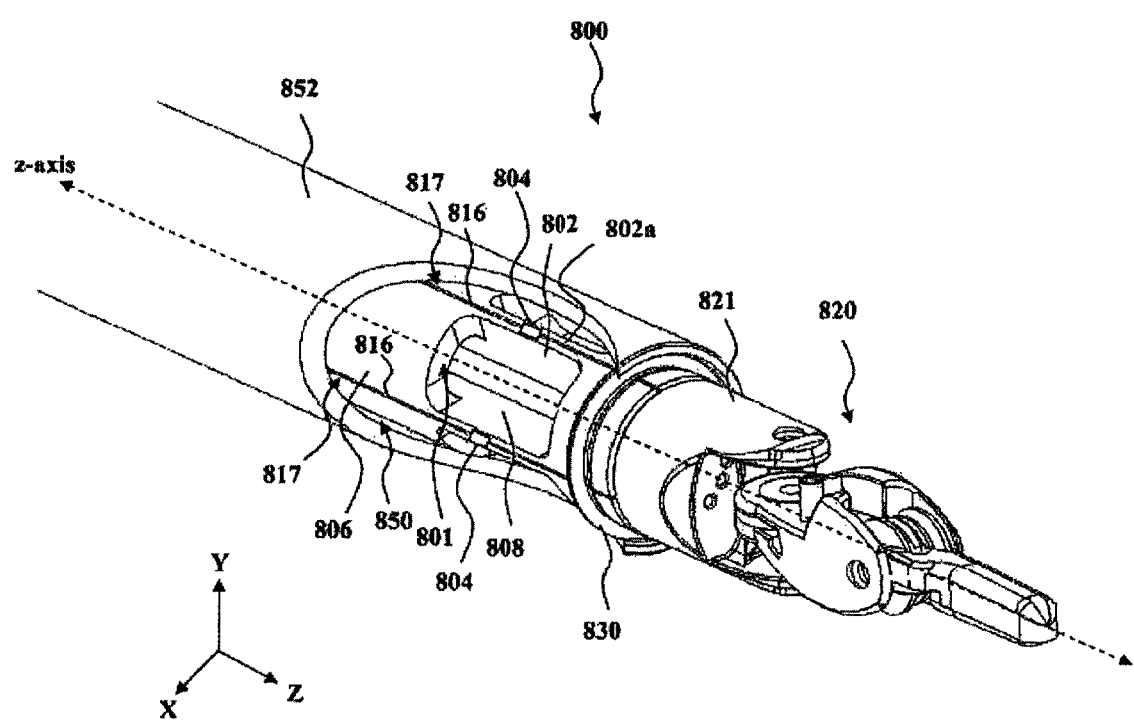
FIG. 10 illustrates a perspective cutaway view of another force sensor apparatus, including apertures exposing radial ribs and a concentric shell surrounding the sensor tube with an annular gap in accordance with an embodiment of the present invention.

Referring now to FIG. 10, a perspective cutaway view of another force sensor apparatus is illustrated in accordance with yet another embodiment. The descriptions of substantially similar parts or elements as those described above with respect to FIGS. 1A-9C are applicable in this embodiment with respect to FIG. 10, although redundant descriptions may be omitted. Force sensor apparatus 800 includes a generally annular tube 806 operably coupled to an end portion 820 via a wrist joint 821. In this embodiment, tube 806 includes a number of rectangular-shaped apertures 801 cut from tube 806 and a plurality of radial ribs 802 forming through passages 808 for passage of wrist actuation cables, wires, tubes, or rods, cautery wires and/or flushing fluids. Ribs 802 run along and radiate from the z-axis centerline of tube 806, and a plurality of strain gauges 804 are oriented parallel to the lengthwise z-axis of the tube and mounted to an outer rib surface 802a. The strain gauges may be inlaid into grooves or a depressed area 817 on the outer rib surface 802a in one example. Wire leads or optic fibers 816 (e.g., shielded twisted pairs, coax, or fiber) coupled to the strain gauges 804 may be inlaid into grooves 817 on the outer rib surface 802a of tube 806. The wire leads or optic fibers 816 may then be embedded in an adhesive bonding or potting compound such as epoxy.

In this embodiment, each of the ribs 802 are separated by 90 degrees measured about the z-axis centerline of tube 806, which forms a cruciform cross-sectional view of the ribs 802. Other separation angles for the ribs are within the scope of the present invention, as outlined above. Furthermore, ribs 802 may extend along the entire length of tube 806 thereby forming internal through passages 808 along the entire length of tube 806, or ribs 802 may extend along a portion(s) of the length of tube 806, thereby forming internal through passages along a portion or portions of the length of tube 806.

Similar to the embodiments described above, force sensor apparatus 800 is capable of sensing bending moments due to lateral forces applied to the wrist joint 821 or its specialized end portion 820. Advantageously, apertures 801 and ribs 802 provide for regions of controlled stress and strain when subjected to bending moments, which may be measured by the fiber optic strain gauges 804 embedded in the grooves 817 along the outer surface of the ribs and sensor body parallel to the lengthwise z-axis of tube 806.

In one example, tube 806 and ribs 802 may be comprised of material with a sufficiently low modulus of elasticity to give a sufficient strain signal under an applied load, a sufficiently high strain at yield to give adequate safety margin above the maximum design load, and a sufficiently high thermal diffusivity to promote rapid thermal equilibrium (therefore reducing thermal disturbances to sensor output signals) when subject to localized or asymmetric thermal disturbances from tissue contact or endoscope illumination. In particular, the plurality of radial ribs 802 may be comprised of a high thermal diffusivity material, such as an aluminum alloy (e.g., 6061-T6 aluminum) or a copper alloy (e.g., GlidCop® AL-60) or silver alloy to reduce the temperature difference between opposing gauges under transient thermal disturbances by providing a direct thermal pathway between opposing gauges. In yet another example, the plurality of fiber optic gauges 804 may be comprised of a negative thermo-optic coefficient optical fiber material, such as phosphate glass fiber, fluoride glass fiber, oxy-fluoride glass fiber, tellurite glass fiber, or a polymer fiber. The negative thermo-optic coefficient fiber advantageously reduces or eliminates the combined effect of a positive thermo-optic coefficient fiber, such as SMF-28 or other doped fiber, and the positive thermal expansion coefficient of the sensor body material.

In one example, tube 806 may be comprised of metal alloys, treated metals, or plated metals, such as of aluminum, copper, or silver, which allow for adequate strain, mechanical failure safety margin, and high thermal diffusivity. In a further example, 6061-T6 aluminum, which is an aluminum alloy that is heat treated and aged, GlidCop® AL-60, which is copper that is dispersion strengthened with ultrafine particles of aluminum oxide, or a dispersion strengthened silver, may be used to form both tube 806 and ribs 802. Accordingly, both the plurality of ribs 802 and the tube 806 may be comprised of a high thermal diffusivity material, such as an aluminum alloy (e.g., 6061-T6 aluminum) or a copper alloy (e.g., GlidCop® AL-60) or silver alloy, to reduce transient and/or steady-state temperature differences between groups of strain gauges separated along the z-axis.

Similar to the embodiment described above with respect to FIGS. 6A-6C1, a thermal shielding may be provided over the strain gauges 804 in accordance with another embodiment. In one example, a thermal shunt shell 852 is provided over tube 806 with an insulating fluid (gas or liquid) filled or evacuated gap 850 being provided between the outer surface of tube 806 and the inner surface of thermal shunt shell 852. Thermal shunt shell 852 may be mechanically and thermally isolated from the strain gauges by providing compliant elastomer rings 830 between the shunt shell 852 and the tube 806 to prevent interference with the applied surgical forces and to insulate the sensor. Thermal shunt shell 852 may be comprised of a high diffusivity material, such as an aluminum alloy (e.g., 6061-T6 aluminum) or a copper alloy (e.g., GlidCop® AL-60) or silver alloy. Optionally, a light reflective surface or coating may be provided over thermal shunt shell 852, which may deflect light and reduce localized heating of the force sensor apparatus, for example from endoscope illumination. An insulating coating may also be provided over thermal shunt shell 852, the insulating coating being comprised of a substantially transparent plastic shrink polymer in one example. Advantageously, the thermal shielding over the strain gauges as described above allows for more uniform heat/thermal diffusion among the sensors, being particularly advantageous for mitigating asymmetric or transient thermal loads upon the instrument. The thermal shielding described above is applicable for various embodiments.

Figure 11A:
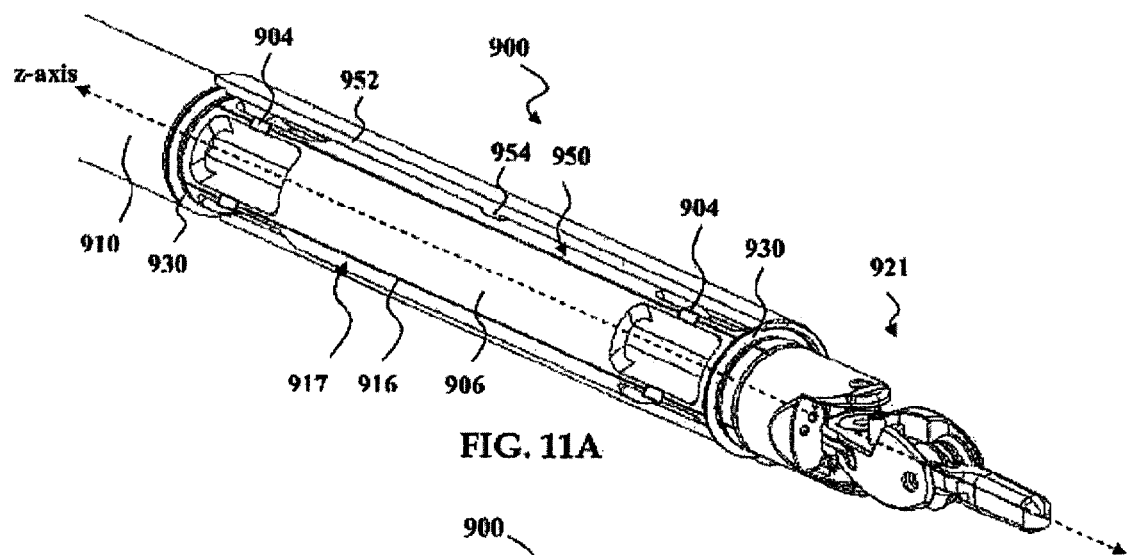
FIGS. 11A-11C illustrate different views of another force sensor apparatus, including a concentric shell surrounding the sensor tube with an annular heat conducting rib in accordance with an embodiment of the present invention.
Figure 11B:
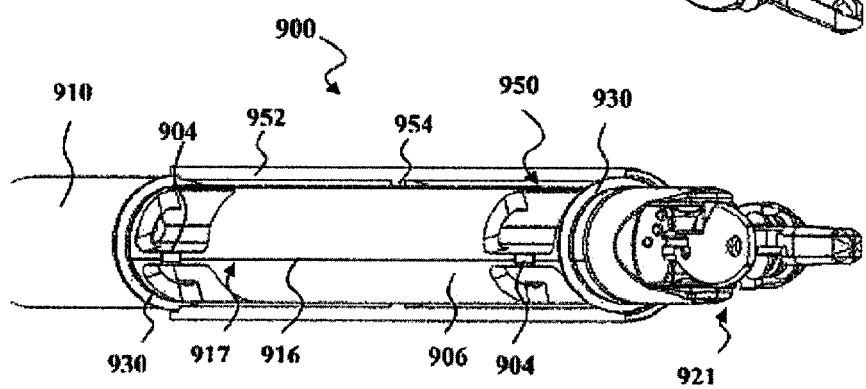
Figure 11C:
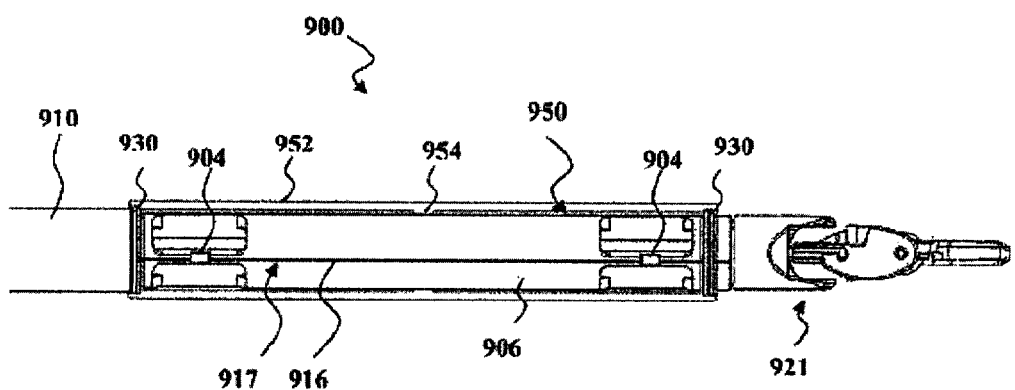

Referring now to FIGS. 11A-11C, different views of another force sensor apparatus is illustrated in accordance with still yet another embodiment. The descriptions of substantially similar parts or elements as those described above with respect to FIGS. 1A-10 are applicable in this embodiment with respect to FIGS. 11A-11C, although redundant descriptions may be omitted. A force sensor apparatus 900 includes a generally annular tube 906 operably coupled to an end effector via a wrist joint 921. In this embodiment, tube 906 includes a plurality of radial ribs forming through passages for passage of wrist actuation cables, wires, tubes, or rods, cautery wires, flushing fluids, and the like. A plurality of strain gauges 904 are oriented parallel to the lengthwise z-axis of the tube and mounted to an outer rib surface. The strain gauges may be inlaid into grooves or a depressed area 917 on the outer rib surface in one example. Wire leads or optic fibers 916 (e.g., shielded twisted pairs, coax, or fiber) coupled to the strain gauges 904 may be inlaid into grooves 917 on the outer rib surface of tube 906. The wire leads or optic fibers 916 may then be embedded in an adhesive bonding or potting compound such as epoxy.

In this embodiment, each of the ribs may be separated by 90 degrees measured about the z-axis centerline of tube 906, which forms a cruciform cross-sectional view of the ribs. Other separation angles for the ribs are within the scope of the present invention, as outlined above. Furthermore, the ribs may extend along the entire length of tube 906 thereby forming internal through passages along the entire length of tube 906, or the ribs may extend along a portion(s) of the length of tube 906, thereby forming internal through passages along a portion or portions of the length of tube 906.

Similar to the embodiments described above, force sensor apparatus 900 is capable of sensing bending moments due to lateral forces applied to the wrist joint or its specialized end portion. Advantageously, the ribs provide for regions of controlled stress and strain when subjected to bending moments, which may be measured by the fiber optic strain gauges 904 embedded in the grooves 917 along the outer surface of the ribs and sensor body parallel to the lengthwise z-axis of tube 906.

In one example, tube 906 and the ribs may be comprised of material with a sufficiently low modulus of elasticity to give a sufficient strain signal under an applied load, a sufficiently high strain at yield to give adequate safety margin above the maximum design load, and a sufficiently high thermal diffusivity to promote rapid thermal equilibrium (therefore reducing thermal disturbances to sensor output signals) when subject to localized or asymmetric thermal disturbances from tissue contact or endoscope illumination. In particular, the plurality of radial ribs may be comprised of a high thermal diffusivity material, such as an aluminum alloy (e.g., 6061-T6 aluminum) or a copper alloy (e.g., GlidCop® AL-60) or a silver alloy to reduce the temperature difference between opposing gauges under transient thermal disturbances by providing a direct thermal pathway between opposing gauges. In yet another example, the plurality of fiber optic gauges 904 may be comprised of a negative thermo-optic coefficient optical fiber material, such as phosphate glass fiber, fluoride glass fiber, oxy-fluoride glass fiber, tellurite glass fiber, or a polymer fiber. The negative thermo-optic coefficient fiber advantageously reduces or eliminates the combined effect of a positive thermo-optic coefficient fiber, such as SMF-28 or other doped fiber, and the positive thermal expansion coefficient of the sensor body material.

In one example, tube 906 may be comprised of metal alloys, treated metals, or plated metals, such as of aluminum, copper, or silver, which allow for adequate strain, mechanical failure safety margin, and high thermal diffusivity. In a further example, 6061-T6 aluminum, which is an aluminum alloy that is heat treated and aged, GlidCop® AL-60, which is copper that is dispersion strengthened with ultrafine particles of aluminum oxide, or a dispersion strengthened silver, may be used to form both tube 906 and the plurality of ribs. Accordingly, both the plurality of ribs and the tube 906 may be comprised of a high thermal diffusivity material, such as an aluminum alloy (e.g., 6061-T6 aluminum) or a copper alloy (e.g., GlidCop® AL-60) or a silver alloy, to reduce transient and/or steady-state temperature differences between groups of strain gauges separated along the z-axis.

Similar to the embodiment described above with respect to FIGS. 6A-6C1, a thermal shielding may be provided over the strain gauges 904 in accordance with another embodiment. In one example, a thermal shunt shell 952 is provided over tube 906 with an insulating fluid (gas or liquid) filled or evacuated gap 950 being provided between the outer surface of tube 906 and the inner surface of thermal shunt shell 952. Thermal shunt shell 952 may be mechanically and thermally isolated from the strain gauges by providing compliant elastomer rings 930 between the shunt shell 952 and the tube 906 to prevent interference with the applied surgical forces and to insulate the sensor.

In this embodiment, thermal shunt shell 952 includes an annular heat conducting rib 954 midway between strain gauges 904 in the axial direction (i.e., the z-axis direction). Heat conducting rib 954 contacts an outer surface of tube 906 and conducts heat from the outer shunt shell to the tube 906 such that external thermal disturbances will be more uniformly diffused among the sensors. In one example, heat conducting rib 954 may be comprised of the same material as thermal shunt shell 952, which may be comprised of a high diffusivity material, such as an aluminum alloy (e.g., 6061-T6 aluminum) or a copper alloy (e.g., GlidCop® AL-60) or a silver alloy. Heat conducting rib 954 may be comprised of a different material than thermal shunt shell 952 in other embodiments but will be comprised of a high thermal diffusivity material. Advantageously, the thermal shielding with heat conducting rib midway between the groups of strain gauges as described above allows for more uniform heat/thermal diffusion among the sensors, being particularly advantageous for mitigating asymmetric or transient thermal loads upon the instrument. The thermal shielding described above is applicable for various embodiments.

Optionally, a light reflective surface or coating may be provided over thermal shunt shell 952, which may deflect light and reduce localized heating of the force sensor apparatus, for example from endoscope illumination. An insulating coating may also be provided over thermal shunt shell 952, the insulating coating being comprised of a substantially transparent plastic shrink polymer in one example.

In some minimally-invasive surgical applications, e.g., teleoperated robotic surgical applications, there may not be sufficient space to implement some of all of the features for the passive thermal rejection strategy. In particular, there may not be space for one or more of the features including a transverse rib coupling diametrically opposite differentially read strain gauges, a thermal shunt shell, an insulating layer between the transducer and the shell, and an insulating coating over the shell.

However, another aspect provides a force sensor apparatus 1200 (FIG. 12A) that has good thermal rejection and can be implemented in a smaller space, when necessary. Force sensor apparatus 1200 with at least one fiber Bragg grating strain gauge simultaneously mitigates or eliminates: (1) effects of varying light polarization on the output of the strain gauge; (2) temperature sensitivity; and (3) calibration drift. Together sensitivity to light polarization, sensitivity to temperature changes, and calibration drift are the most significant problems associated with measuring force using an optic fiber Bragg grating strain gauge. This single solution to eliminate or at least to mitigate all three effects represents a significant advance in force sensors using an optic fiber Bragg grating strain gauge. Of course, if only one or a subset of these factors is of importance for a particular application of the force sensor, the force measurement is improved by mitigating or eliminating the factor or factors of importance.

Figure 12A:
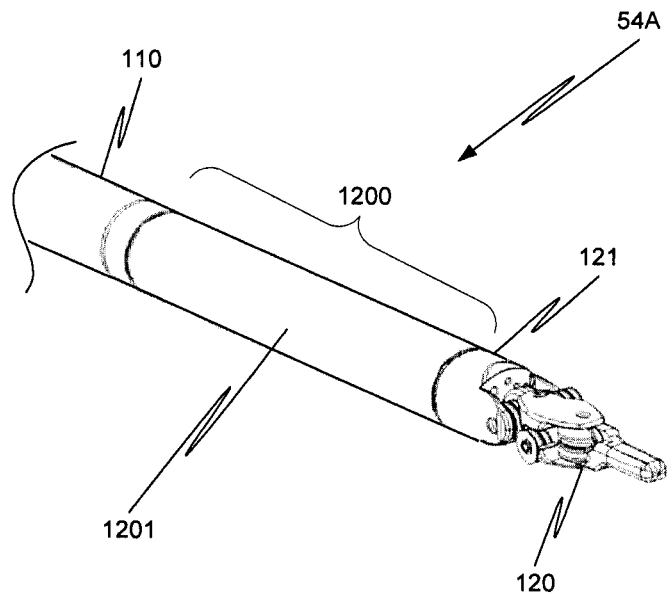
FIGS. 12A-12D illustrate different views of another force sensor apparatus including a polarization and temperature insensitive surgical instrument force transducer in accordance with an embodiment of the present invention.

In this aspect, this novel force sensor apparatus 1200 is implemented in surgical instrument assembly 54A (FIG. 12A). Surgical instrument assembly 54A is similar to surgical instrument assembly 54 (FIG. 2), as described above, with the exception that force sensor apparatus 100 is replaced with force sensor apparatus 1200.

Force sensor apparatus 1200 is operably coupled to a distal end of rigid instrument shaft 110 that was described above and operably coupled proximal to a wrist joint 121 that also was described above. End effector portion 120, as described above, is coupled to force sensor apparatus 1200 via wrist joint 121. In one example, the diameter of force sensor apparatus 1200 matches the diameter of instrument shaft 110, thus allowing the entire assembly of the instrument (including the coupled force sensor apparatus 1200) to pass through a cannula or a seal without added friction or snagging.

Figure 12B:
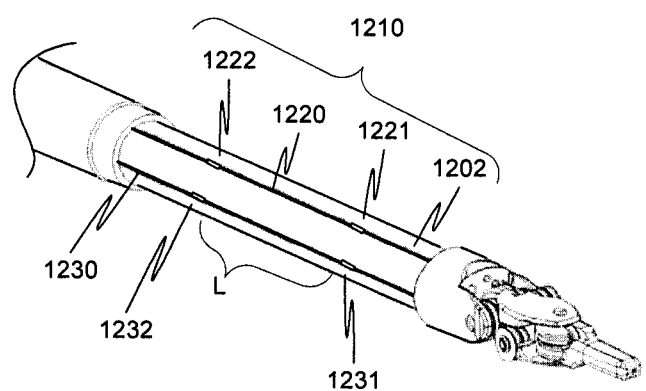

FIG. 12B shows a perspective view of force sensor apparatus 1200 with cover 1201, sometimes called sleeve 1201 or thermal shunt shell 1201, removed. In one aspect, cover 1201 is made of a material with high thermal diffusivity so that cover 1201 remains at a substantially uniform temperature because the material dissipates temperature gradients quickly. In one aspect, cover 1201 is made of the same metal as transducer body 1202 of force transducer 1210.

In this aspect, force transducer 1210 includes a transducer body 1202. Fixedly mounted in grooves along the outer circumferential surface of transducer body 1202 are a plurality of optic fibers including optic fibers 1220, 1230, 1240, 1250 (optic fibers 1240 and 1250 are not visible in FIG. 12B, but see FIG. 12D). Each optic fiber 1220, 1230 includes at least one fiber Bragg grating 1221, 1231 that functions as a strain gauge.

In one aspect, the fiber Bragg grating is written into a phosphate glass optic fiber with high intensity pulses from a 193 nm wavelength ArF excimer laser with a phase mask. See for example, J. Albert et al., "Strong Bragg Gratings in Phosphate Glass Single Mode Fiber," *Appl. Phys. Letters* 89, 101127 (2006). Multiple fiber Bragg gratings can be written into an optic fiber if the fiber Bragg gratings are formed in such a way as to use different wavelengths. This is a particularly useful property for an embodiment with a double ring of strain gauges as only four fibers are embedded into metal transducer body 1202, each with two fiber Bragg gratings separated by a known distance, e.g., fiber Bragg grating 1231 and fiber Bragg grating 1232 separated by known distance L (FIG. 12B).

An interrogator unit 334 (FIG. 5E) decodes the optically encoded strain information from force transducer 1210 into electrical signals compatible with the computer control hardware 340 of the robotic surgical system. A processor is used to calculate forces according to the equations outlined in U.S. Patent Application Publication No. 2007/0151390 A1, entitled "Force and Torque Sensing for Surgical Instruments," of Stephen J. Blumenkranz, et al., published on Jul. 5, 2007 for U.S. patent application Ser. No. 11/537,241, which was incorporated herein by reference above.

As explained more completely below, the output signals from force transducer 1210 are polarization and temperature insensitive relative to conventional force sensors that utilize fiber Bragg gratings as strain gauges. Transducer body 1202 has a coefficient of thermal expansion. Each of the plurality of optic fibers 1220, 1230, 1240 and 1240 is selected so that the coefficient of thermal expansion of the optic fiber matches the coefficient of thermal expansion of transducer body 1202.

As used herein, "match" does not mean an exact numerical equality between two parameters. Rather, herein "match" means that given (i) a set of first parameters, where the set may include one or more members and each of member in the set has a different value, and (ii) a second parameter, the first parameter with the smallest difference between that first parameter and the second parameter is said to be the first parameter that matches the second parameter.

To illustrate this definition of a match, two different examples are considered. In a first example, consider a set of optic fibers including fiber Bragg gratings, where the set includes at least two such optic fibers and the first parameter is a coefficient of thermal expansion. Each of optic fibers in the set has a different coefficient of thermal expansion. The second parameter is the coefficient of thermal expansion of transducer body 1202 In this example "match" means that given a set of at least two optic fibers including fiber Bragg gratings, where each optic fiber in the set has a different coefficient of thermal expansion, the optic fiber with the smallest difference between the coefficient of thermal expansion of transducer body 1202 and the coefficient of thermal expansion of that optic fiber is said to be the optic fiber with a coefficient of thermal expansion that matches the coefficient of thermal expansion of transducer body 1202.

In a second example, consider a set of optic fibers including fiber Bragg gratings, where the set includes at least two such optic fibers and the first parameter is a normalized thermo-optic coefficient. Each of the optic fibers in the set has a different normalized thermo-optic coefficient. The second parameter is the coefficient of thermal expansion of transducer body 1202 In this example "match" means that given a set of at least two optic fibers including fiber Bragg gratings, where each optic fiber in the set has a different normalized thermo-optic coefficient, the optic fiber with the smallest sum of the coefficient of thermal expansion of transducer body 1202 and the normalized thermo-optic coefficient of that optic fiber is said to be the optic fiber with a normalized thermo optic coefficient that matches the coefficient of thermal expansion of transducer body 1202. The match that eliminates the effect of transducer body thermal expansion occurs when the optic fiber normalized thermo-optic coefficient is negative and has an absolute value equal to the transducer coefficient of thermal expansion.

In addition to using an optic fiber with a coefficient of thermal expansion that matches the coefficient of thermal expansion of the transducer body to reduce polarization sensitivity and creep induced calibration drift effects, better thermal performance is obtained with an optic fiber that has a negative thermo-optic coefficient. For such an optic fiber, the fiber Bragg grating negative thermal effect counters the transducer body positive thermal expansion effect providing reduced net transducer thermal sensitivity.

Finally, in one aspect, each optic fiber with a fiber Bragg grating is fixedly attached to transducer body 1202 using an adhesive that also has a coefficient of thermal expansion. The adhesive used is selected based on a match between the coefficient of thermal expansion of the adhesive and the coefficient of thermal expansion of the fiber and body. Again, match is interpreted as defined above. In addition, as explained more completely below, among adhesives with the appropriate properties, such as high hardness, the adhesive with the highest glass transition temperature is selected. The other aspects of force sensor apparatus 1200 for mating with instrument shaft 110 and wrist joint 121 are similar to those described above for force sensor apparatus 100 and so are not repeated, but are incorporated herein by reference.

Figure 12C:
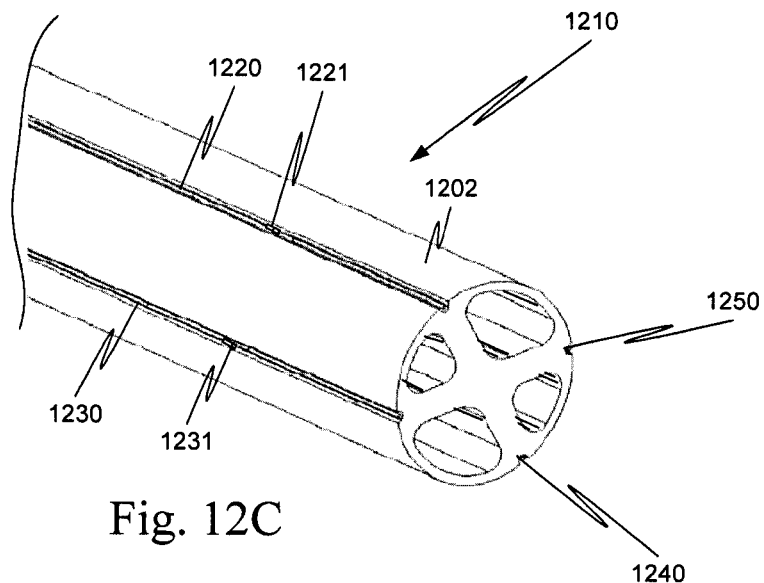
Figure 12D:
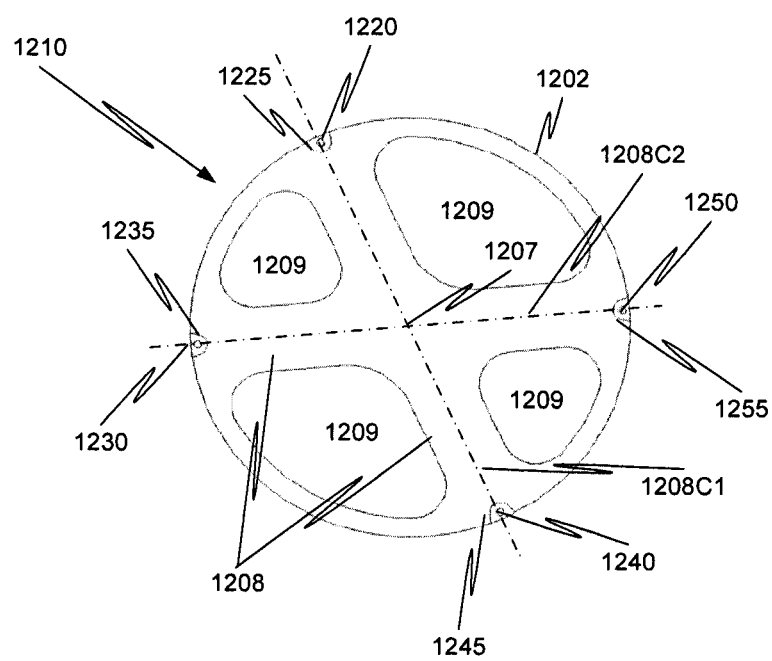

As illustrated in FIGS. 12C and 12D, in this example, transducer body 1202 includes a plurality of radial ribs 1208 forming through passages 1209 for passage of actuation cables, wires, tubes, rods, cautery wires and/or flushing fluids. Ribs 1208 run along and radiate from the z-axis centerline 1207 of transducer body 1202. A number (e.g., 3, 4, 6, or 8) of fiber Bragg gratings in optic fibers 1220, 1230, 1240, 1250 are oriented parallel to the lengthwise z-axis, sometimes called the longitudinal axis, of transducer body 1202.

Optic fibers 1220, 1230, 1240, 1250 are inlaid into grooves 1225, 1235, 1245, 1255, respectively, formed on an outer cylindrical surface of transducer body 1202. In this example, a groove extends straight along and parallel to the z-axis of transducer body 1202. In other aspects, the groove, for example, could be a helix in the outer cylindrical surface around the z-axis of transducer body 1202.

In this example, transverse centerlines 1208C1, 1208C2 for a rib also intersect the centerlines of corresponding grooves. Optic fibers 1220, 1230, 1240, 1250 may be inlaid into matching grooves in shaft 110 of the surgical instrument 54A. Optic fibers 1220, 1230, 1240, 1250 may then be embedded in an adhesive bonding or potting compound such as epoxy.

As disclosed in U.S. Patent Application Publication No. 2007/0151390 A1 on Jul. 5, 2007 for U.S. patent application Ser. No. 11/537,241, filed Sep. 29, 2006, the contents of which have been previously incorporated by reference, fiber Bragg gratings may be spaced in a ring at intervals around the circumference of the transducer body 1202 (e.g., 3 gauges at 120 degrees, 4 gauges at 90 degrees, or 4 gauges at 70 degrees and 110 degrees or other pairs of supplementary angles). The signals from the fiber Bragg gratings are combined arithmetically in various sums and differences to obtain measures of transverse forces $F_x$ and $F_y$ (FIG. 3A) exerted upon the instrument tip and to reject axial force $F_z$ and the torques $T_x$ and $T_y$ about the two axes perpendicular to the shaft axis (i.e., axes x and y).

The measurement of the forces is made independent of the orientation and effective lever arm length of articulated wrist joint 121 at the distal end of the instrument when two axially separated sets or rings of fiber Bragg gratings are utilized and their signals are subtracted. Forces exerted against end portion 120 are detected by Bragg fiber gratings via interrogator 334 (FIG. 5E), which may be operably coupled to the servo control or to processor 340 (FIG. 5E) for notifying the surgeon of these forces (e.g., via master(s) or a display). It is understood that by adding a second ring of similarly oriented gauges (e.g., two sets of 3 gauges or two sets of 4 gauges) at a different lengthwise axial position on transducer body 1202, additional load-induced bending moment information may be obtained, and dependence of the transverse force data $F_x$, $F_y$ on instrument wrist length, orientation, and resulting jaw distance may be eliminated.

In a further embodiment, three stain gauges 120 degrees apart may be used to form a set instead of four stain gauges 90 degrees apart. Thus, combinations of strain gauges may include a single ring of three gauges 120 degrees apart, two rings of three gauges each 120 degrees apart (i.e., a total of six gauges), a single ring of four gauges 90 degrees apart, and two rings of four gauges each 90 degrees apart (i.e., a total of eight gauges). Single ring strain gauge embodiments may be useful for non-wristed tools such as probes. Strain gauges may also be oriented on the surface of shaft 110 at angles that permit recovery of the additional torque signal $T_z$ about the shaft axis.

As just described, fiber Bragg gratings (FBG) may be advantageous in that two sensing elements may be located along one optic fiber at a known separation L, thereby only requiring the provision of four fibers on transducer body 1202 for eight gauges. As indicated above, a Bragg grating is written into the optic fiber with a laser.

The fiber Bragg grating (FBG) is a spatial periodicity of variation in the refractive index along the axis of the optic fiber. Light entering the fiber Bragg grating is preferentially reflected at a particular wavelength (Bragg wavelength $\lambda_B$) that is a function of the refractive index and the period of the index variation. Other wavelengths pass through the fiber Bragg grating unchanged. To measure strain, broad spectrum infrared (IR) light is sent down the optic fiber and the wavelength of the reflection from the fiber Bragg grating indicates the strain so that the fiber Bragg grating functions as a strain gauge.

Figure 13:
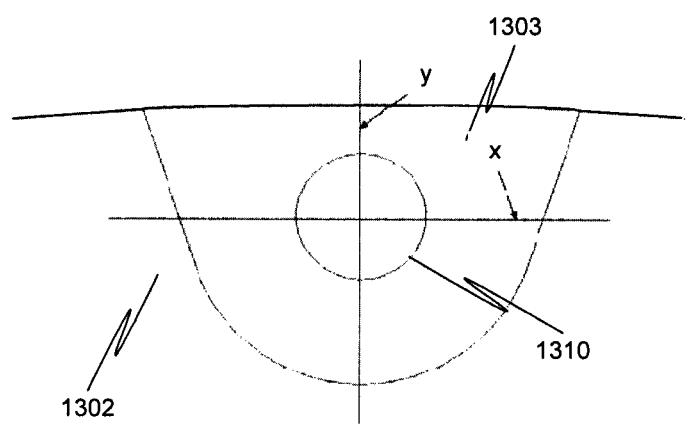
FIG. 13 illustrates strain axes for a force transducer.

Prior to considering force transducer 1210 in further detail, limitations on measurements with a conventional force transducer utilizing a fiber Bragg grating are considered. As shown in FIG. 13, about axis y, fiber 1310 has body 1302 on both sides. However, about axis x, fiber 1310 has body 1302 on only one side.

When the transducer body, fiber and adhesive contract as they cool after elevated temperature curing of the adhesive bond in the groove, the transverse strains on optic fiber 1310, and consequently the fiber Bragg grating, are different in the x- and y-symmetry directions. Thus, the strain optic effect induces a different index of refraction in the x- and y-planes of optic fiber 1310. This is called bi-refringence and makes the fiber Bragg grating exhibit a different reflected wavelength for light polarized in one or the other of the strain directions. Because the Bragg reflection wavelength peaks overlap for common fiber Bragg grating designs with typical amounts of induced bi-refringence, the effect is blended for light polarized at angles between the x and y directions. The summed wavelength peak shifts as the light polarization angle rotates.

Interrogator 334 typically provides polarized light. However, flex and twist of the optic fiber cable connecting interrogator 334 to the fiber Bragg grating(s) may cause the polarization angle of the light to rotate. Due to the different transverse strains in the x- and y-directions and the resulting different indexes of refraction in the two corresponding planes, the fiber Bragg grating reflects a varying wavelength peak as the fiber optic cable bends and twists rotating the polarization angle. When the fiber optic cable is routed through the links of a moving robot arm or routed loose through the air to a force sensing surgical instrument mounted on a moving robot arm the shifting fiber Bragg grating strain gauge outputs result in unpredictable variations in the measured force on the instrument transducer.

Hence, unequal transverse strains $\epsilon_x$ and $\epsilon_y$ (FIG. 13) on the fiber Bragg grating (caused by differential thermal contraction of body 1302, optic fiber 1310 and adhesive 1303, after elevated temperature curing of the adhesive) induce birefringence in the optic fiber core and split the reflected Bragg wavelength into two overlapping peaks corresponding to the two principal transverse strain directions in the fiber Bragg grating. Further bending and twisting of the optic fiber leading to the fiber Bragg grating affect the rotation of the polarization angle of light transmitted to the fiber Bragg grating, and the apparent load induced wavelength shift also changes as the maximum reflected signal shifts between one peak and the other.

Force sensor apparatus 1200 includes a force transducer 1210, which minimizes or eliminates the polarization and temperature sensitivity compared to conventional force transducers with fiber Bragg grating. The definition of the wavelength of light $\lambda_B$ reflected by a fiber Bragg grating is:

$$\lambda_B(T,\epsilon) = 2 * \eta * \Lambda$$

where $\lambda_B(T,\epsilon)$ is the Bragg wavelength,
T is the temperature,
$\epsilon$ is strain,
$\eta(T,\epsilon)$ is the fiber core refractive index, and
$\Lambda(T,\epsilon)$ is the Bragg grating period.

The change of Bragg wavelength $\lambda_B$ with respect to temperature is the partial derivative of Bragg wavelength $\lambda_B$ with respect to temperature, which is:

$$\frac{\partial \lambda_B}{\partial T} = 2 * \left( \eta \frac{\partial \Lambda}{\partial T} + \Lambda \frac{\partial \eta}{\partial T} \right), \quad (1)$$

$$\frac{\partial \lambda_B}{\partial T} = 2 * \eta * \Lambda * \left( \frac{1}{\Lambda} \frac{\partial \Lambda}{\partial T} + \frac{1}{\eta} \frac{\partial \eta}{\partial T} \right) = \lambda_B * \left( \frac{1}{\Lambda} \frac{\partial \Lambda}{\partial T} + \frac{1}{\eta} \frac{\partial \eta}{\partial T} \right).$$

where $$\frac{\partial \eta}{\partial T} = \text{thermo-optic coefficient } (TOC)$$

of the fiber core (some publications give TOC normalized to the index of refraction as $$\frac{1}{\eta} \frac{\partial \eta}{\partial T}$$

and so care is required in the use of published data),
and where, $$\frac{1}{\Lambda} \frac{\partial \Lambda}{\partial T} = \text{coefficient of thermal expansion } (CTE).$$

The coefficient of thermal expansion of the transducer body 1202 dominates when an optic fiber is bonded to the body. If the optic fiber is not bonded to a transducer body, the coefficient of thermal expansion is that of the optic fiber itself.

Similarly, the change of Bragg wavelength $\lambda_B$ with respect to strain is the partial derivative of Bragg wavelength $\lambda_B$ with respect to strain $\epsilon$, which is:

$$\frac{\partial \lambda_B}{\partial \epsilon} = 2 * \left( \eta \frac{\partial \Lambda}{\partial \epsilon} + \Lambda \frac{\partial \eta}{\partial \epsilon} \right),$$

$$\frac{\partial \lambda_B}{\partial \epsilon} = 2 * \eta * \Lambda * \left( \frac{1}{\Lambda} \frac{\partial \Lambda}{\partial \epsilon} + \frac{1}{\eta} \frac{\partial \eta}{\partial \epsilon} \right) = \lambda_B * \left( \frac{1}{\Lambda} \frac{\partial \Lambda}{\partial \epsilon} + \frac{1}{\eta} \frac{\partial \eta}{\partial \epsilon} \right).$$

This is sometimes cast as $$\Delta\lambda_B = \lambda_B * \left(1 - \frac{\eta^2}{2}[p_{12} - v*(p_{11} + p_{12})]\right) * \varepsilon = \lambda_B * (1 - p_e) * \varepsilon,$$

where $p_e$ is the effective strain optic coefficient. The following discussion of compensation for thermal effects relies only on the first equation above for the thermal sensitivity $$\frac{\partial \lambda_B}{\partial T}.$$

Thus, at least two factors are considered in making force transducer 1210: (i) the difference in coefficients of thermal expansion for the body of force transducer 1210 and the optic fiber used; and (2) the thermal sensitivity of the combination of the combination of the body and the optic fiber. Thus, a material for the body must be chosen and then the best optic fiber for that body chosen. Of course, this process could be done in the reverse fashion also-choose the optic fiber and then select the best body material for that fiber.

Thus, the properties of a representative set of optic fibers are considered and then the properties of representative materials, i.e., metals, for the body are considered. This is followed by demonstrating the advantages of matching the coefficients of thermal expansion and controlling the thermo-optic coefficient. Specifically, the properties of a conventional force transducer implemented using silica optic fiber is compared with force transducer 1210 implemented using phosphate glass optic fiber and various metal alloy bodies. Finally, a method for making an embodiment of force transducer 1210 is presented.

In the following examples, the Bragg grating periods are based on a reflected Bragg wavelength of 1550 nm in optic fiber with the respective core refractive indexes. Table 1 presents properties of a commercially available silica optic fiber called SMF-28 available from Corning Inc. of Corning N.Y.

TABLE 1

Properties of Corning SMF-28 silica optic fiber with Bragg grating with a $\lambda_B$ of 1550 nm

| | |
|---|---|
| Core Refractive Index, $\eta$ | 1.468 |
| Coeff. of Thermal Expansion, CTE | $0.56 \times 10^{-6}/°$ C. |
| Thermo-optic coefficient, $\frac{\partial \eta}{\partial T}$ | $12 \times 10^{-6}/°$ C. |
| Bragg Grating Period, $\Lambda$ | 528 nm |

Table 2 presents properties of three phosphate glass optic fibers based on measured properties of phosphate glass formulations called 88c, 106a and 126a by Schafer Corp. of Albuquerque, N. Mex. See for example, William A. Goodman, "Phosphate Athermal Glass for Windows and Fibers— Phase II SBIR Contract HQ0006-05-C-7255," 2006 Mirror Technology Days, Kirtland Air Force Base, Albuquerque, N. Mex. (2006).

TABLE 2

Properties of phosphate glass optic fibers with Bragg grating with a $\lambda_B$ of 1550 nm

| Phosphate glass formulation | 88c | 106a | 126a |
|---|---|---|---|
| Core Refractive Index, $\eta$ | 1.526 | 1.569 | 1.588 |
| Coeff. of Thermal Expansion, CTE | $17.8 \times 10^{-6}/°$ C. | $14.7 \times 10^{-6}/°$ C. | $15.2 \times 10^{-6}/°$ C. |
| Thermo-optic Coeff. (at 1.54 μm) Schott, $\frac{\partial \eta}{\partial T}$ | $-13.2 \times 10^{-6}/°$ C. | $-12 \times 10^{-6}/°$ C. | $-12.4 \times 10^{-6}/°$ C. |
| Bragg Grating Period, $\Lambda$ | 508 nm | 494 nm | 488 nm |

The above examples of phosphate glass optic fibers with negative thermal-optic coefficients are illustrative only and are not intended to be limiting. In view of this disclosure, other optic fibers with a negative thermal-optic coefficient can be used. Suitable optic fibers include, but are not limited to, a fluoride glass fiber, an oxy-fluoride glass fiber, and a tellurite glass fiber.

In the following examples, transducer body 1202 is metal. In one example, the metal making up transducer body 1202 may be selected from a group including metal alloys, treated metals, or plated metals, such as of aluminum, stainless steel, maraging steel, or titanium, which allow for adequate strain at yield to permit a high strain signal to noise ratio while providing required mechanical failure safety margin. More specifically, the metal is selected from metals including an aluminum alloy, a stainless steel alloy, a maraging steel alloy and a titanium alloy. Yet more specifically, the metal is selected from a group of metals including tempered (aged and optionally strain relieved) 2000 series, 6000 series and 7000 series aluminum alloys, precipitation hardened stainless steel alloys, quench hardened stainless steel alloys, age hardened maraging steel alloys, and titanium alloys in annealed or solution treated and aged condition.

As is known to those knowledgeable in the field, the percentage by weight of a particular element in an alloy is expressed as a number and may be given as a range or as a mean value in the manufacturer's datasheet. The name of such a metal alloy may often be based on a nominal or approximate mean value of the range of the chief alloying elements. As an example, the titanium alloy known as Ti-6Al-4V is stated to contain 5.5% to 6.75% of aluminum and 3.5% to 4.5% of vanadium. In another example, the stainless steel alloy known as 17-4PH is stated to contain 15.0% to 17.5% of chromium and 3.0% to 5.0% of nickel. The percentages of alloying elements used in alloys or in alloy categories as stated herein include the ranges or the mean values stated in representative manufacturer's data sheets.

The 2000, 6000 and 7000 series of aluminum alloys are commercially available and have specified compositions and tempering treatments including solution annealing, aging and strain relieving. The designation and classification of these alloys according to their primary alloying elements and treatments is governed by the International Alloy Designation System (IADS) introduced in 1970 and derived from the standards of the Aluminum Association of the United States. Traces of other elements may also be present in these alloys and do not conflict with the classification system. In each case the balance of the alloy after addition of the alloying elements is aluminum.

In the IADS system, the alloy composition of suitable 2000 series aluminum alloys is currently distinguished by a predominant copper content of between 1.8% and 6.8%. At the same time, 2000 series aluminum alloys may be further enhanced by addition of magnesium of up to 1.9% by weight. Other suitable aluminum alloys containing more or less copper and/or magnesium may be developed and added to this 2000 classification in the future.

Also in the IADS system, the alloy composition of suitable 6000 series aluminum alloys is currently distinguished by a predominant magnesium content of between 0.6% and 1.3% by weight in conjunction with a silicon content of between 0.4% and 1.8% by weight. Other suitable aluminum alloys containing more or less of magnesium and/or silicon may be developed and added to this 6000 classification in the future.

In another category of the IADS system, the alloy composition of suitable 7000 series aluminum alloys is currently distinguished by a predominant Zinc content of between 3.5% and 8.4% by weight in conjunction with a magnesium content of between 0.8% and 3.4% by weight with further additions of copper between 0.3% and 2.6% by weight. Other suitable aluminum alloys containing more or less of zinc, magnesium and/or copper may be developed and added to this 7000 classification in the future.

Other suitable aluminum alloys that fall outside the IADS system include those made by rapid solidification as metglass (metals with glassy non-crystalline structure) followed by comminution, compaction and sintering to result in alloys with exceedingly fine microstructure and high strength. These rapid solidification metglass based aluminum alloys are currently distinguished by a predominant zinc content of 5.0% to 11.5% by weight in conjunction with magnesium content of up to 2.5% by weight with further additions of copper up to 1.5% by weight. Examples of such alloys include, but are not limited to, RSA-706, RSA-707, RSA-708 and RSA-709 aluminum alloys manufactured by RSP Technology BV of The Netherlands. Other suitable metglass aluminum alloys containing more or less of zinc, magnesium and/or copper may be developed and added to this category in the future.

Representative aluminum alloys of high strain at yield include, but are not limited to, 2024/2124, 2091, 2014, 2048, 2090, 6041, 6066, 6262, 6033, 7010, 7076, 7050, 7055, 7075/7175/7475, 7049/7149, 7001, 7068, RSA706, RSA-707, RSA-708 and RSA-709 aluminum alloys. The composition of most such aluminum alloys may be found in The Aluminum Industry Standards of the Aluminum Association in Registration Record Series Teal Sheets, February 2009 or in the manufacturer's datasheets. See also for example, "Alloy 7075, Understanding Cold Finished Aluminum Alloys, Alcoa Cold Finished Products," Massena N.Y. Copyright May, 2004.

Aluminum alloys are tempered to obtain high strength values. As an example, T-6 tempering for 7075 aluminum alloy is solution heat treating and thermal aging as defined in the datasheets of the manufacturers or in the standards. T-6 aged 7075 aluminum alloy has a stated ultimate tensile strength of 77,000 psi (530 MPa) and a yield strength of 66,000 psi (455 MPa).

Aluminum alloys such as 7075 aluminum alloy, which are stress relieved by stretching after solution treating and then aged, are designated T651. This process mitigates unintended loss of straightness or shape as material is removed during machining. Material undergoing further minor straightening is designated T6511.

Such refinements to tempering and other differing combinations of these refinements including cold work, compressive yielding and the like apply to other aluminum alloys also. Reference to aluminum alloys herein may be by the alloy number alone and is understood to comprise suitable temper for the best strength and stability. Aluminum alloy and temper designations, chemical composition limits and registered properties in North America, all originate from the system of American National Standards Institute (ANSI) and Aluminum Association (AA) standards and so are known.

Precipitation and quench hardenable stainless steels are also called martensitic stainless steels. The alloy composition of these stainless steels predominantly includes 10.0% to 18.0% of Chromium by weight and in the case of the precipitation hardening grades may also include 3.0% to 11.5% of Nickel by weight. Generally lesser amounts of Molybdenum may also be included as well as of Copper, Aluminum or Titanium affecting hardening or corrosion resistance. Traces of other elements with maximum limits may also be present and do not conflict with the hardenability of these alloys. In each case the balance of the alloy after the alloying and trace elements is iron.

Representative precipitation hardenable stainless steel alloys of high strain at yield include, but are not limited to, 13-8 (UNS S13800), 15-5 (S15500), 15-7 (S15700), 17-4 (S17400), 17-7 (S17700), 450 (S45000), 455 (S45500), 465 (S46500) and 475 stainless steel alloys. Representative quench hardenable stainless steel alloys include, but are not limited to, 410 (S41000), 416 (S41600), 420 (S42000), 440A/440B/440C (S44002/3/4 resp.) and Questek S53 (AMS 5922) stainless steel alloys.

The composition of such stainless steel alloys may be found in the data sheets of manufacturers including AK Steel, Carpenter Technology, QuesTek and others. There are one or more of Unified Numbering System for Metals & Alloys (UNS), American Iron & Steel Institute (AISI), Society of Automotive Engineers (SAE), Aerospace Material Specification (AMS), American Society of Mechanical Engineers (ASME) and American Society for Testing and Materials (ASTM) designations and specifications for these stainless steel alloys.

As an example, precipitation hardening of 17-4 (UNS S17400) stainless steel alloy to condition H900 requires solution treating by heating to 1900° F. (1040° C.) for one-half hour followed by cooling below 90° F. (32° C.) and then thermal aging by heating to 900° F. (480° C.) for one hour as described in the manufacturer's datasheets. H900 aged 17-4 stainless steel has a stated ultimate tensile strength of 198,000 psi (1365 MPa) and a yield strength of 183,000 psi (1260 MPa). Stainless steel alloy and temper designations, chemical composition limits and registered properties in North America, all originate from the system of AISI, SAE, UNS, ASTM, AMS and American National Standards Institute (ANSI) standards and so are known.

A family of maraging steel alloys includes those made predominantly with 18.0-19.0% of nickel. Such alloys may also contain between 7.5% and 12.0% of cobalt although some may contain no cobalt. These maraging steels also contain molybdenum in quantities ranging from 3.0% to 5.1% and titanium in quantities ranging from 0.2% to 1.85%.

Another family of maraging steels includes those made with 11% to 12% of nickel. Such alloys may also contain between 13.4% and 15.6% of cobalt, between 2.3% and 3.1% of chromium and between 1.2% and 1.9% of molybdenum.

Maraging steels are distinguished by a combination of high strength with high toughness. Representative maraging steels include C-200, C-250 (UNS K92890), C-300 (UNS K93120), C-350, T-200, T-250, T-300, AerMet® 100, AerMet® 310 and AerMet® 340. (AerMet® is a U.S. registered trademark of Carpenter Technology Corporation of Wyomissing, Pa., U.S.A.) Such alloys attain high strength by a combination of solution annealing which may be done at 1500° F. (815° C.) followed by air cooling to room temperature and then by elevated temperature aging at temperatures in the range of 850° F. (455° C.) to 950° F. (510° C.). Such alloys are available from companies such as ATI-Allvac and Carpenter Technology.

Titanium alloys include four families: (1) commercially pure, (2) alpha/near alpha, (3) alpha-beta, and (4) beta types. The commercially pure grades of titanium alloys are of lower strength insufficient for a compact force transducer subjected to high stresses.

Titanium alloys are often referred to by grade numbers, chief alloy constituent percentages, UNS numbers or AMS specifications. Not all titanium alloys have grade numbers. Herein, the names containing the alloy constituents or the UNS numbers are used to refer to titanium alloys. In addition, titanium alloys may be differentiated by heat treatment used to enhance their formability or strength. Titanium alloys are provided in annealed condition wherein the strength is lower but formability is higher and also in solution treated and aged (STA) condition wherein strength is maximized. The strength attained in the STA condition may be reduced at larger diameters or thicknesses. Values referred to herein are for sizes suited for manufacture of a medical instrument force transducer.

As an example of naming according to alloy constituents, the Ti-6Al-4V (UNS R56400) titanium alloy contains 5.5% to 6.75% of aluminum (Al) and 3.5% to 4.5% of vanadium (V) by weight. Ti-6Al-4V titanium alloy has a yield strength of 120,000 psi (827 MPa) in the annealed condition and, for bar under ½ inch diameter, a yield strength of 155,000 psi (1070 MPa) in the STA condition. The STA condition of Ti-6Al-4V titanium alloy is achieved by first solution treating the alloy at 1725-1775° F. (940-970° C.) for ten minutes followed by water quench. The alloy is then aged at 900-1100° F. (480-595° C.) for two to eight hours and air cooled.

The modulus of elasticity of titanium alloys varies with alloying constituents. Since the modulus of elasticity of this Ti-6Al-4V titanium alloy is $16.5 \times 10^6$ psi (114 GPa), the strain at yield is given by $$155,000/16,500,000 = 9.39 \times 10^{-3} = 9390 \,\mu\varepsilon.$$

Thus, a force transducer can be designed for a high strain value at an adequate factor of safety with Ti-6Al-4V STA titanium alloy.

Other titanium alloys with strain at yield in the higher strength STA condition, or in the annealed condition for some, suitable for a medical instrument force transducer include Ti-6Al-4V ELI (UNS R56401), Ti-3Al-2.5V (R56320), Ti-6Al-6V-2Sn (R56620), Ti-6Al-2Sn-4Zr-2Mo (R54620, R54621), Ti-5Al-2.5Sn (R54520), Ti-6Al-2Sn-4Zr-6Mo (R56260), and Ti-38-6-44 (R58640) titanium alloys. The titanium alloy Ti-6Al-4V-ELI (UNS R56401) with reduced impurities may be used for human implants. These are titanium alloys of alpha-beta, beta, or alpha/near alpha types with aluminum content ranging from 3% to 6% nominally, e.g., 2.5% to 6.75% permitted by alloying tolerances.

The published coefficient of thermal expansion for aluminum alloys ranges from $22.9 \times 10^{-6}$/° C. to $23.9 \times 10^{-6}$/° C. The value for 7075 aluminum alloy of $23.4 \times 10^{-6}$/° C. is therefore representative for the discussion below. The coefficient of thermal expansion for 17-4 stainless steel is $10.8 \times 10^{-6}$/° C. while other stainless steel alloys mentioned above are also close to this value. The coefficients of thermal expansion for maraging steel alloys fall into two groups with coefficients of thermal expansions of $10.1 \times 10^{-6}$/° C. and $12.8 \times 10^{-6}$/° C. respectively with C-300 having a representative value for discussion of $10.1 \times 10^{-6}$/° C. The coefficient of thermal expansion of the titanium alloys discussed above ranges from $7.7 \times 10^{-6}$/C to $9.6 \times 10^{-6}$/C with Ti-6Al-4V titanium alloy at $8.6 \times 10^{-6}$/C being a suitable example for the discussion below.

Prior to considering various examples of body materials and optic fibers, consider the partial derivative of Bragg wavelength $\lambda_B$ with respect to temperature for only a silica optic fiber with the properties of Table 1.

$$\frac{\partial \lambda}{\partial T} = \lambda_B * \left( \frac{1}{\Lambda} \frac{\partial \Lambda}{\partial T} + \frac{1}{\eta} \frac{\partial \eta}{\partial T} \right)$$
$$= 1550 \text{ nm} * [0.56 \times 10^{-6}/° \text{ C.} +$$
$$(12 \times 10^{-6}/° \text{ C.})1.468]$$
$$= 13.5 \text{ pm}/° \text{ C.}$$

Thus, the calculated thermal sensitivity of the Bragg reflection wavelength in a bare silica optic fiber including a fiber Bragg grating is 13.5 picometers per degree Centigrade. Comparable published values range from 10 pm/° C. to 13.5 pm/° C. for this fiber.

As a first example, consider a body 1202 made of 7075-T6 aluminum alloy. In this example, a set of optic fibers includes a silica optic fiber with the properties of Table 1, and a phosphate glass optic fiber with the properties of the 88c phosphate glass optic fiber in Table 2. The use of two optic fibers is illustrative only and is not intended to limit the set of optic fibers considered to any particular number.

As a first differential criterion, a comparison for each fiber in the set is done with the coefficient of thermal expansion of 7075-T6 aluminum alloy. Specifically, a coefficient of thermal expansion difference is determined for each fiber, where $$CTE \text{ diff} = CTE \text{ metal} - CTE \text{ fiber} \qquad (2)$$
$$CTE \text{ diff (Silica)} = (23.4 \times 10^{-6}/° \text{ C.}) -$$
$$(0.56 \times 10^{-6}/° \text{ C.})$$
$$= 22.8 \times 10^{-6}/° \text{ C.}$$

$$CTE \text{ diff (Phosphate)} = (23.4 \times 10^{-6}/° \text{ C.}) -$$
$$(17.8 \times 10^{-6}/° \text{ C.})$$
$$= 5.6 \times 10^{-6}/° \text{ C.}$$

The result of the first differential criterion is to select the phosphate glass optic fiber because the coefficient of thermal expansion of the phosphate glass optic fiber matches the coefficient of thermal expansion of 7075-T6 aluminum alloy, which is used as a representative of aluminum alloys, better than the thermal expansion of the silica glass optic fiber matches the coefficient of thermal expansion of 7075-T6 aluminum alloy. Therefore, the coefficient of thermal expansion of the phosphate glass optic fiber is said to match the coefficient of thermal expansion for aluminum alloys. The selection of the phosphate glass optic fiber results in approximately 75% reduction in the differential thermal contraction after elevated temperature adhesive cure, e.g., $$((22.8 - 5.6)/22.8) * 100 = 75\%.$$

With the phosphate glass optic fiber, the induced transverse strain due to post cure cool down and thermal contraction and the resulting polarization sensitivity of Bragg gratings in the phosphate glass optic fiber on an aluminum body are reduced in comparison to Bragg gratings in a silica optic fiber on a similar aluminum body. Similarly, the reduced induced longitudinal strain reduces calibration drift in the phosphate glass optic fiber on an aluminum body in comparison to a silica optic fiber on a similar aluminum body.

In another aspect, the thermal sensitivity, which is analyzed using $$\frac{\partial \lambda}{\partial T}$$

as defined above, is also used to select the optic fiber. The thermal sensitivity of the transducer considers the effect of the thermo-optic coefficient of the fiber core and the transducer thermal expansion of the bonded transducer and fiber assembly dominated by the coefficient of thermal expansion of the transducer body. The thermal sensitivity is determined for each optic fiber in the set and the selection based on thermal expansion coefficients is further evaluated.

Silica Optic Fiber with Fiber Bragg Grating on 7075-T6 Aluminum Alloy Body $$\frac{\partial \lambda}{\partial T}(\text{silica} \& 7075) = \lambda_B * \left(\frac{1}{\Lambda}\frac{\partial \Lambda}{\partial T} + \frac{1}{\eta}\frac{\partial \eta}{\partial T}\right)$$
$$= 1550 \text{ nm} * (23.4 \times 10^{-6}/°\text{ C.} +$$
$$(1/1.468 * 12 \times 10^{-6}/°\text{ C.})$$
$$= 49.0 \text{ pm}/°\text{ C.}$$

Phosphate Glass Optic Fiber with Fiber Bragg Grating on 7075-T6 Aluminum Alloy Body $$\frac{\partial \lambda}{\partial T}(\text{phosphate} \& 7075) = \lambda_B * \left(\frac{1}{\Lambda}\frac{\partial \Lambda}{\partial T} + \frac{1}{\eta}\frac{\partial \eta}{\partial T}\right)$$
$$= 1550 \text{ nm} * (23.4 \times 10^{-6}/°\text{ C.} +$$
$$(1/1.526 * (-13.2 \times 10^{-6}/°\text{ C.})]$$
$$= 22.9 \text{ pm}/°\text{ C.}$$

Thus, the selection of the phosphate glass optic fiber reduces the thermal sensitivity by 53%, ((49.0−22.9)/49.0)*100=53%

In the above example, a 7075 aluminum alloy body was used as an example of an aluminum alloy body. This example is illustrative only and is not intended to be limiting. For example, a 7068 aluminum alloy body was used and results similar to those just described for the 7075 aluminum alloy body were obtained with a phosphate glass optic fiber.

As another example, consider a force transducer with a stainless steel body 1202 and a phosphate glass optic fiber with a fiber Bragg grating. This force transducer is compared to a force transducer having an aluminum alloy transducer body with a silica glass optic fiber. A stainless steel alloy representative of the stainless steel alloys, discussed above, is 17-4 stainless steel.

A force transducer with the combination of the phosphate glass optic fiber and a 17-4 stainless steel transducer body reduces, after cure, the differential thermal contraction and polarization sensitivity on the order of 69% in comparison to the force transducer with the silica optic fiber on aluminum alloy substrate (the effects of the adhesive bond line are again not considered), e.g., (((23.4−0.56)−(17.8−10.8))/(23.4−0.56))*100=69%

Phosphate Glass Optic Fiber with Fiber Bragg Grating on 17-4 Stainless Steel Alloy Transducer Body $$\frac{\partial \lambda}{\partial T}(\text{phosphate} \& 17-4) = \lambda_B * \left(\frac{1}{\Lambda}\frac{\partial \Lambda}{\partial T} + \frac{1}{\eta}\frac{\partial \eta}{\partial T}\right)$$
$$= 1550 \text{ nm} * (10.8 \times 10^{-6}/°\text{ C.} +$$
$$(1/1.526 * (-13.2 \times 10^{-6}/°\text{ C.})]$$
$$= 3.3 \text{ pm}/°\text{ C.}$$

Thus, the thermal sensitivity is reduced from 49.0 pm/° C. for silica optic fiber on the aluminum alloy body to 3.3 pm/° C. The selection of the phosphate glass optic fiber with the 17-4 stainless steel body results in a thermal sensitivity reduced by 93%, ((49.0−3.3)/(49.0))*100=93%.

The combination of a phosphate glass fiber and a stainless steel alloy body not only provides enhanced performance, but also reduces the need for the ribs and other features described above to implement a passive thermal rejection strategy. Thus, this combination allows use of force transducers in applications that were previously not practical due to the physical size of the force sensor apparatus.

As a further example, consider a force transducer with a maraging steel alloy body 1202 and a phosphate glass optic fiber with a fiber Bragg grating. This force transducer is compared to a force transducer having an aluminum alloy transducer body with a silica glass optic fiber. A maraging steel alloy representative of the maraging steel alloys, discussed above, is C-300 maraging steel.

A force transducer with the combination of the phosphate glass optic fiber and a C-300 maraging steel alloy transducer body reduces, after cure, the differential thermal contraction and polarization sensitivity on the order of 66% in comparison to the force transducer with the silica optic fiber on aluminum alloy substrate (the effects of the adhesive bond line are again not considered), e.g., (((23.4−0.56)−(17.8−10.1))/(23.4−0.56))*100=66%

Phosphate Glass Optic Fiber with Fiber Bragg Grating on C-300 Maraging Steel Alloy Transducer Body $$\frac{\partial \lambda}{\partial T}(\text{phosphate} \& C-300) = \lambda_B * \left(\frac{1}{\Lambda}\frac{\partial \Lambda}{\partial T} + \frac{1}{\eta}\frac{\partial \eta}{\partial T}\right)$$
$$= 1550 \text{ nm} * (10.1 \times 10^{-6}/°\text{ C.} +$$
$$(1/1.526 * (-13.2 \times 10^{-6}/°\text{ C.})]$$
$$= 2.2 \text{ pm}/°\text{ C.}$$

Thus, the thermal sensitivity is reduced from 49.0 pm/° C. for silica optic fiber on the aluminum alloy body to 2.2 pm/° C. The selection of the phosphate glass optic fiber with the C-300 maraging steel alloy body results in a thermal sensitivity reduced by 95%, ((49.0−2.2)/(49.0))*100=95%.

The combination of a phosphate glass fiber and a maraging steel alloy body not only provides enhanced performance, but also reduces the need for the ribs and other features described above to implement a passive thermal rejection strategy. Thus, this combination allows use of force transducers in applications that were previously not practical due to the physical size of the force sensor apparatus.

As yet another example, consider a force transducer with a titanium alloy body 1202 and a phosphate glass optic fiber with a fiber Bragg grating. This force transducer is compared to a force transducer having an aluminum alloy transducer body with a silica glass optic fiber. A titanium alloy representative of the titanium alloys, discussed above, is Ti-6Al-4V.

A force transducer with the combination of the phosphate glass optic fiber and a Ti-6Al-4V titanium alloy transducer body 1202 reduces, after cure, the differential thermal contraction and polarization sensitivity on the order of 60% in comparison to the force transducer with the silica optic fiber on aluminum alloy substrate (the effects of the adhesive bond line are again not considered), e.g., (((23.4−0.56)−(17.8−8.6))/(23.4−0.56))*100=60%

Phosphate Glass Optic Fiber with Fiber Bragg Grating on Ti-6Al-4V Titanium Alloy Transducer Body $$\frac{\partial \lambda}{\partial T}(\text{phosphate \& } Ti-6Al-4V) = \lambda_B * \left(\frac{1}{\Lambda}\frac{\partial \Lambda}{\partial T} + \frac{1}{\eta}\frac{\partial \eta}{\partial T}\right)$$

$$= 1550 \text{ nm} * (8.6 \times 10^{-6}/° \text{ C.} +$$

$$(1/1.526*(-13.2 \times 10^{-6}/° \text{ C.})]$$

$$= -0.1 \text{ pm}/° \text{ C.}$$

Thus, the thermal sensitivity is reduced from 49.0 pm/° C. for silica optic fiber on the aluminum alloy body to −0.1 pm/° C. The selection of the phosphate glass optic fiber with the Ti-6Al-4V titanium alloy body results in a thermal sensitivity reduced by 99.8%, ((49.0−0.1)/(49.0))*100=99.8%.

This combination not only provides enhanced performance, but also reduces the need for the ribs and other features described above to implement a passive thermal disturbance rejection strategy. Thus, this combination allows use of force transducers in applications that were previously not practical due to the physical size of the force sensor apparatus.

Thus, as shown above, at least the difference between the coefficient of thermal expansion of the optic fiber and the coefficient of thermal expansion of transducer body 1202 is considered. This selection reduces or eliminates polarization shift induced variation of force output from fiber Bragg grating force sensors. In addition, in one aspect, the thermal sensitivity is also considered in the optic fiber selection, and in particular an optic fiber having a negative thermo-optic coefficient is selected. A force sensor utilizing a fiber Bragg grating in an optic fiber having a negative thermo-optic coefficient reduces the force transducer sensitivity to temperatures changes between the operating room and the human body in addition to the simultaneous advantage of polarization shift insensitivity due to the matched coefficients of thermal expansion.

In one aspect, a method 1400 is utilized in making force transducer 1210. Method 1400 is a method for reducing temperature and polarization effects for an optic fiber Bragg grating strain gauge based surgical instrument force transducer by selective choice and application of transducer body material and strain sensing fiber material.

Method 1400 transforms a transducer body and a set of optic fibers of differing materials having fiber Bragg gratings into a novel strain gauge based surgical instrument force transducer. Alternatively, method 1400 can transform an optic fiber with at least one fiber Bragg grating and a set of transducer bodies of differing materials into a novel strain gauge based surgical instrument force transducer. Method 1400 can also transform a set of transducer bodies of differing materials and a set of optic fibers of differing materials having fiber Bragg gratings into a novel strain gauge based surgical instrument force transducer.

Figure 14:
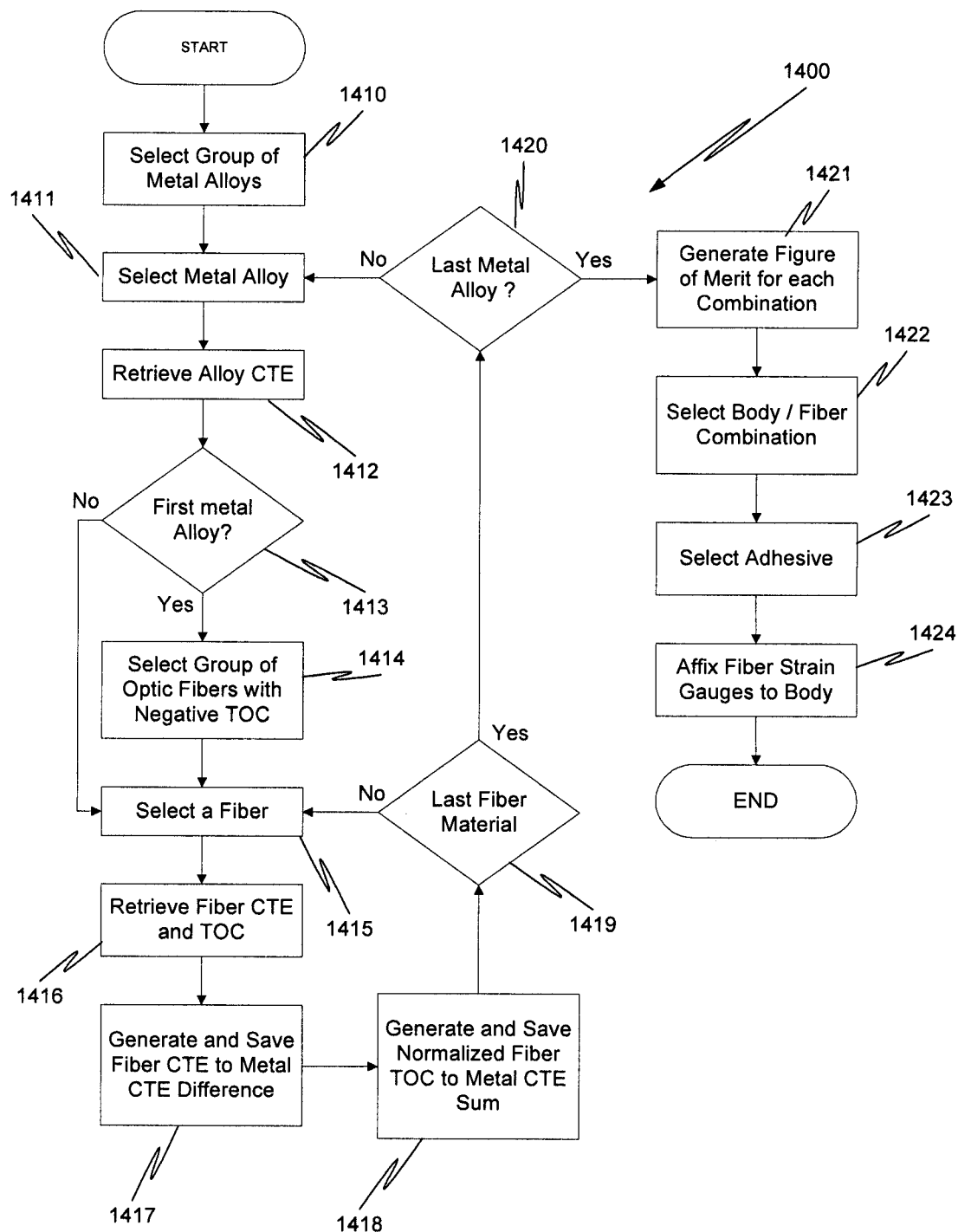
FIG. 14 is a process flow diagram for making the polarization and temperature insensitive surgical instrument force transducer in FIGS. 12A to 12D in accordance with an embodiment of the present invention.

Referring to FIG. 14, upon starting method 1400, potential materials for ribs 1208, if used, and transducer body 1202 are selected in SELECT GROUP OF METAL ALLOYS operation 1410. As used herein a group includes a least one member. However, a group can also include sub-groups that in turn include at least one member. Thus, in one example, the members in the group selected could all be alloys of a particular metal, e.g., aluminum. In another example, the group selected could include subgroups of metal alloys, e.g., aluminum alloys, stainless steel alloys and titanium alloys, where each subgroup included at least one alloy of the metal. Factors that go into the selection of the group of metal alloys may include the metal alloy's suitability for use in a medical instrument as well as the characteristics of the metal alloy with respect to suitability for making a force transducer. Processing transfers from operation 1410 to SELECT METAL ALLOY operation 1411.

In SELECT METAL ALLOY operation 1411, one of the metal alloys in the group of metal alloys is selected. Upon completion of SELECT METAL ALLOY operation 1411, RETRIEVE ALLOY COEFFICIENT OF THERMAL EXPANSION operation 1412 obtains the coefficient of thermal expansion for the metal alloy selected.

Upon completion of operation 1412, FIRST METAL ALLOY check operation 1413 determines whether the metal alloy being processed is the first metal alloy considered. If the metal alloy is the first metal alloy, check operation 1413 transfers processing to SELECT GROUP OF OPTIC FIBERS WITH NEGATIVE THERMAL OPTIC COEFFICIENTS operation 1414 and otherwise transfers processing to SELECT A FIBER operation 1415.

A group of optic fibers with Bragg gratings and a negative thermo-optic coefficient are selected in operation 1414. For example, the group of optic fibers in Table 2 could be selected. The group of optic fibers includes at least one optic fiber. Herein, optic fibers with a negative thermo-optic coefficient are used. Also, in one aspect, the optic fibers have higher coefficients of thermal expansion that a conventional silica fiber. However, method 1400 can be used for optic fibers that do not have a negative thermo-optic coefficient, if such fibers are of interest.

SELECT FIBER operation 1415 selects one fiber from the group for processing and processing transfers to RETRIEVE COEFFICIENT OF THERMAL EXPANSION AND THER- MAL OPTIC COEFFICIENT operation 1416, which retrieves the two coefficients for the selected fiber. Processing transfers from operation 1416 to GENERATE AND SAVE FIBER COEFFICIENT OF THERMAL EXPANSION (CTE) TO METAL COEFFICIENT OF THERMAL EXPANSION(CTE) DIFFERENCE operation 1417.

Operation 1417 generates a difference between the metal alloy coefficient of thermal expansion and the optic fiber coefficient of thermal expansion as defined in expression (2), above. The difference is saved in a table. In one aspect, the difference is saved in a difference column a table in a row with an index representing the metal alloy and optic fiber combination. When all the optic fibers and metal alloys have been processed, the smallest difference in the difference column of the table gives the best match between the coefficients of thermal expansion of the optic fiber and the metal alloy. Processing transfers from operation 1417 to GENERATE AND SAVE NORMIALIZED FIBER THERMO-OPTIC COEFFICIENT(TOC) TO METAL COEFFICIENT OF THERMAL EXPANSION(CTE) SUM operation 1418.

Operation 1418 generates a sum of the optic fiber normalized thermo-optic coefficient (See definition above following expression (1)) and the metal alloy coefficient of thermal expansion as defined in expression (1), above. The sum is saved in the table containing the differences just described. Specifically, the sum is saved in a sum column in the row having the index representing the metal alloy and optic fiber combination. When all the optic fibers and metal alloys have been processed, the smallest sum in the sum column of the table gives the best match between the thermo-optic coefficient of the optic fiber and coefficient of thermal expansion of the metal alloy. Processing transfers from operation 1418 to operation 1419.

LAST FIBER MATERIAL check operation 1419 determines whether all the optic fibers in the group selected in operation 1414 have been processed. If all the optic fibers have been processed, check operation 1419 transfers to LAST METAL ALLOY check operation 1420 and otherwise to SELECT A FIBER operation 1415. Operations 1415 to 1419 are repeated until all the optic fibers in the group have been processed.

LAST METAL ALLOY check operation 1420 determines whether all the metal alloys in the group selected in operation 1410 have been processed. If not all of the metal alloys have been processed, check operation 1420 transfers to SELECT METAL ALLOY operation 1411 and otherwise to GENERATE FIGURE OF MERIT FOR EACH COMBINATION operation 1421. Operations 1411 to 1420 are repeated until all the metal alloys in the group have been processed.

When the desired range of transducer body and optic fiber materials have been considered (including instances of a single body material and a range of fiber materials or vice versa) in operations 1410 to 1420, a figure of merit is then generated, in operation 1421, as a basis for comparing the relative desirability of the different combinations. This figure of merit may be a simple arithmetic sum (equal weighting) or square root sum of squares combination of calculated force signal level variations due to polarization and thermal effects as represented by the difference and sum, respectively, in the table for the particular optic fiber material and metal alloy combination. It may also be an un-equally weighted sum (including a zero weighting of a term such as ignoring an effect) of the two effects, e.g., where average error magnitudes of the two effects while the respective effects are acting are multiplied by the time weighted prevalence of the two effects. Other weighting factor values and types may also be used. The effect of creep induced calibration drift or other effect may similarly be introduced in a weighted combination scheme of another figure of merit. After a figure of merit is generated for each combination in the table, processing transfers from operation 1421 to operation 1422.

In SELECT BODY/FIBER COMBINATION operation 1422, the combination of metal alloy and optic fiber with the best figure of merit is selected for the force transducer. The best figure of merit is dependent on the definition of the figure of merit. Specifically, if the figure of merit is used to minimize the effects, the smallest figure of merit is the best. Conversely, if a reciprocal of the minimization is used as the figure of merit, the largest figure of merit is the best.

After selection of the body material and the optic fiber based on the figure of merit in operation 1422, an adhesive is selected in SELECT ADHESIVE process 1423. In one aspect, two factors are considered in the selection of an adhesive, the coefficient of thermal expansion of the adhesive and the glass transition temperature of the adhesive. In another aspect, only one of the two factors is considered.

In process 1423, an adhesive is selected with the closest possible coefficient of thermal expansion match to the coefficients of thermal expansion of transducer body 1202 and the optic fibers to reduce transverse strain on the fiber Bragg grating after cool down from curing the adhesive. In addition to the base resin choice for the adhesive, the adhesive coefficient of thermal expansion may be further reduced by addition of low coefficient of thermal expansion powdered materials (e.g. silica flour) to the extent permitted by thixotropy which may interfere with adequate adhesive flow and wetting.

In one aspect, operations 1410 to 1423 are performed by a processor executing instructions stored in a memory. In this aspect, the table and at least one of the figures of merit are also stored in the memory.

Finally, as indicated above, in AFFIX FIBER STRAIN GAUGES TO BODY process 1424, the selected optic fibers with the fiber Bragg gratings are embedded in the grooves in the selected metal alloy body 1202 with the adhesive. The adhesive is cured at a temperature below the glass transition temperature of the adhesive to solidify the adhesive fully. Then, post-cure above an autoclaving temperature of 270° F. (132° C.) is completed without inducing further cool down strain in the fiber Bragg grating and bond greater than the strain due to the initial cure. To facilitate process 1424, the adhesive selected has the highest possible glass transition temperature consistent with other required properties.

Creep induced calibration drift occurs when unequal post-cure axial contraction of the optic fiber and transducer body result in residual shear stress in the adhesive between the optic fiber and transducer body 1202. The adhesive may then undergo slow shear deformation creep over an extended period of time as well as more rapid creep at elevated temperatures encountered during autoclaving the surgical instrument containing force transducer 1210. However, the closer match of the coefficients of thermal expansion of transducer body 1202 and optic fibers 1220, 1230, 1240, 1250 reduces axial shear stress in the adhesive bond of the optic fiber to transducer body 1202, thus reducing the tendency of the transducer calibration to drift due to creep in the adhesive bond layer.

Using process 1400 to make a force transducer 1210 with an aluminum alloy body and a phosphate glass optic fiber with a fiber Bragg grating results in a significant advance over a similar force transducer with a silica glass optic fiber. As demonstrated above, force transducer 1210 with an aluminum alloy body and a phosphate glass optic fiber simultaneously mitigates or eliminates: (1) effects of varying light polarization on the output of the strain gauge; (2) temperature sensitivity; and (3) calibration drift.

Making force transducers according to process 1400 reduces or eliminates polarization shift induced change of force output from fiber Bragg grating force sensors; reduces or eliminates thermal sensitivity in a fiber Bragg grating based force sensor; and reduces or eliminates creep induced calibration drift. Hence, the problems that previously limited fiber Bragg grating based force sensors have been eliminated, or at least greatly mitigated so that such sensors can be used in a wider variety of applications and can be made smaller and less costly by eliminating features used to implement a passive thermal rejection strategy.

Embodiments described above illustrate but do not limit the invention. It should also be understood that numerous modifications and variations are possible in accordance with the principles of the present invention. Accordingly, the scope of the invention is defined only by the following claims.

I claim:

1. A surgical instrument comprising:
   a force sensor apparatus, operatively mounted in said surgical instrument, comprising a force transducer, wherein the force transducer comprises:
      a transducer body having a coefficient of thermal expansion; and
      at least one optic fiber fixedly attached to the transducer body, wherein the at least one optic fiber includes a Bragg grating, wherein the at least one optic fiber has a coefficient of thermal expansion, wherein the at least one optic fiber has a negative thermo-optic coefficient, wherein the at least one optic fiber having the negative thermo-optic coefficient is a phosphate glass optic fiber, and wherein the coefficient of thermal expansion of the transducer body and the coefficient of thermal expansion of the at least one optic fiber are matched to mitigate polarization and calibration drift effects on said force transducer.

2. The surgical instrument of claim 1, wherein said transducer body comprises a stainless steel alloy.

3. The surgical instrument of claim 2 wherein said stainless steel alloy comprises 10% to 18% of chromium by weight.

4. The surgical instrument of claim 2 wherein said stainless steel alloy is a precipitation hardened stainless steel alloy comprising 10% to 18% of chromium and 3.0% to 11.5% of nickel by weight.

5. The surgical instrument of claim 1 wherein said at least one optic fiber is fixedly attached to said transducer body by an adhesive.

6. The surgical instrument of claim 5 wherein said adhesive has a coefficient of thermal expansion matched to said coefficient of thermal expansion of said at least one optic fiber and to said coefficient of thermal expansion of said transducer body.

7. The surgical instrument of claim 6 wherein said adhesive has a glass transition temperature and when said at least one optic fiber is affixed to said transducer body by said adhesive, said adhesive is cured at a temperature less than said glass transition temperature and then post-cured above the glass transition temperature and above an autoclaving temperature.

8. The surgical instrument of claim 1 wherein said transducer body includes a groove formed in an outer surface of said transducer body and said at least one optic fiber is fixedly attached in said groove of said transducer body.

9. The surgical instrument of claim 8 wherein said groove is a straight groove substantially parallel to a longitudinal axis of said transducer body.

10. A surgical instrument comprising:
    a force sensor apparatus, operatively mounted in the surgical instrument, comprising a force transducer, wherein the force transducer comprises:
       a transducer body having a coefficient of thermal expansion; and
       at least one optic fiber fixedly attached to the transducer body, wherein the at least one optic fiber includes a Bragg grating, wherein the at least one optic fiber has a coefficient of thermal expansion, wherein the at least one optic fiber has a negative thermo-optic coefficient, wherein the at least one optic fiber having the negative thermo-optic coefficient is a fluoride optic fiber, and wherein the coefficient of thermal expansion of the transducer body and the coefficient of thermal expansion of the at least one optic fiber are matched to mitigate polarization and calibration drift effects on the force transducer.

11. A surgical instrument comprising:
    a force sensor apparatus, operatively mounted in the surgical instrument, comprising a force transducer, wherein the force transducer comprises:
       a transducer body having a coefficient of thermal expansion; and
       at least one optic fiber fixedly attached to the transducer body, wherein the at least one optic fiber includes a Bragg grating, wherein the at least one optic fiber has a coefficient of thermal expansion, wherein the at least one optic fiber has a negative thermo-optic coefficient, wherein the at least one optic fiber having the negative thermo-optic coefficient is an oxy-fluoride optic fiber, and wherein the coefficient of thermal expansion of the transducer body and the coefficient of thermal expansion of the at least one optic fiber are matched to mitigate polarization and calibration drift effects on the force transducer.

* * * * *